US006699687B1

(12) United States Patent
Tsien et al.

(10) Patent No.: US 6,699,687 B1
(45) Date of Patent: Mar. 2, 2004

(54) CIRCULARLY PERMUTED FLUORESCENT PROTEIN INDICATORS

(75) Inventors: Roger Y. Tsien, La Jolla, CA (US); Geoffrey Baird, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/316,920

(22) Filed: May 21, 1999

(51) Int. Cl.[7] .................. C12N 15/12; C12N 15/63; C12N 15/00; C07K 14/00; C07H 21/04
(52) U.S. Cl. .................. 435/69.1; 435/320.1; 435/325; 530/350; 536/23.5
(58) Field of Search .................. 530/350; 435/69.1, 435/320.1, 325; 536/23.5

(56) References Cited

U.S. PATENT DOCUMENTS

| | | | |
|---|---|---|---|
| 4,603,209 A | 7/1986 | Tsien et al. | 548/236 |
| 5,049,673 A | 9/1991 | Tsien et al. | 546/107 |
| 5,439,797 A | 8/1995 | Tsien et al. | 435/7.21 |
| 5,958,713 A | 9/1999 | Thastrup et al. | 435/69.1 |

OTHER PUBLICATIONS

Graf et al. Random circular permutation. Proc. Natl. Acad. Sci. USA. 93:11591–11596 (1996).*
Miyawaki et al., "Fluorescent indicators for $Ca^{2+}$ based on green fluorescent proteins and calmodulin," *Nature* 388:882–887 (1997).
Romoser et al., "Detection in Living Cells of $Ca^{2+}$–dependent Changes in the Fluorescence Emission of an Indicator Composed of Two Green Fluorescent Protein Variants Linked by a Calmodulin–binding Sequence," *The Journal of Biological Chemistry*, 272(20):13270–13274 (1997).
Abedi, et al., Genetic insertion of peptides into pre–selected regions of GFP, *Nucl. Acids Res.*, 26:623–630 (1998).
Graf, et al., Random circular permutation, *Proc. Natl. Acad.*, 93:11591–11596 (1996).

* cited by examiner

*Primary Examiner*—Gary Kunz
*Assistant Examiner*—Joseph F. Murphy
(74) *Attorney, Agent, or Firm*—Heller Ehrman White & McAuliffe LLP

(57) ABSTRACT

The present invention provides polypeptide and polynucleotides encoding fluorescent indicators having inserted within a fluorescent moiety a sensor polypeptide. Also provided are methods of using the fluorescent indicator. Circularly permuted fluorescent polypeptides and polynucleotides are also provided.

19 Claims, 8 Drawing Sheets

YFP, Calmodulin Insertion Sequence Summary

MVSKGEE........LEYNGGTMHDQLT........QMMTAKEL NSHNVY......MDELYK

YFP Nter    YFP    Cam Nter                  Cam Cter    YFP    YFP Cter
                   Linker                    Linker

YFP, Zif Insertion Sequence Summary

MVSKGEE........LEYNGGTRPYACPVESCDRRFSRSDELTRHIRIHTGEL NSHNVY......MDELYK

YFP Nter    YFP    Zif Nter                                      Zif Cter    YFP    YFP Cter
                   Linker                                        Linker

FIG. 1

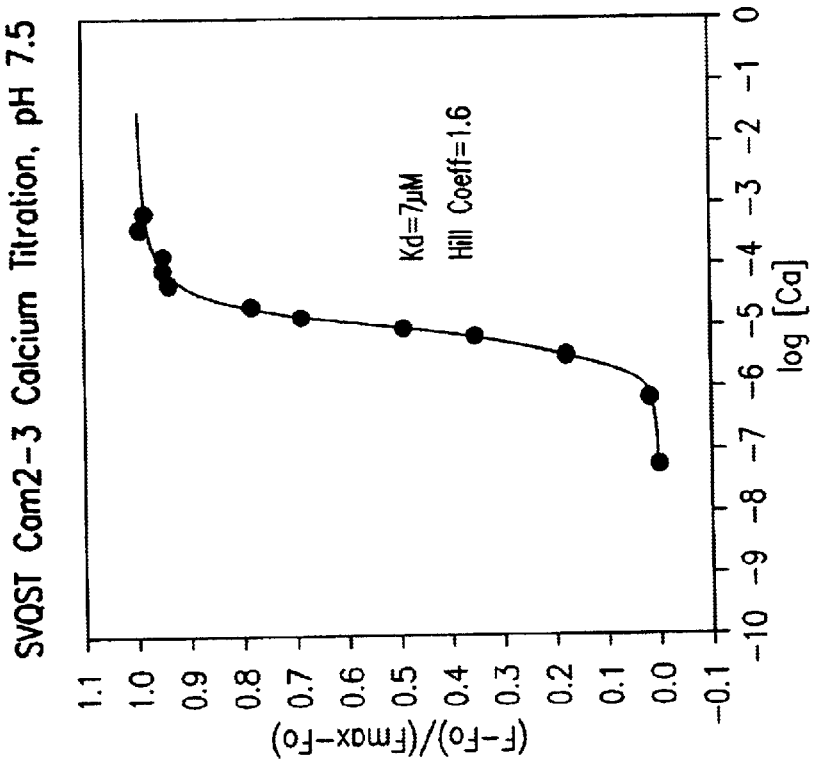
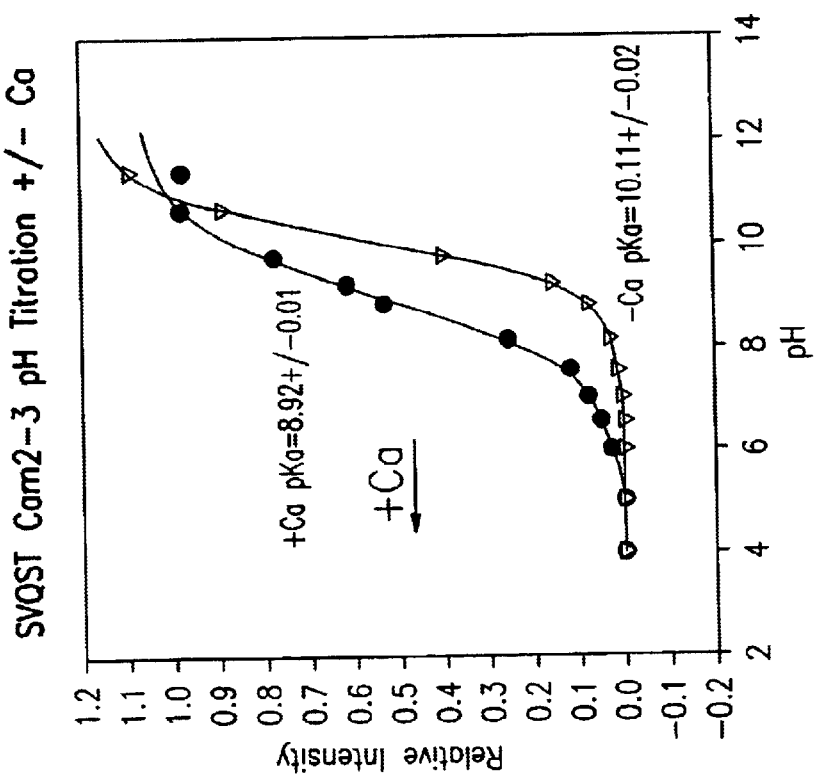
FIG. 2B
FIG. 2A

Random Circular Permutation 2
- Digest With DNAse, $Mn^{2+}$
- Repair Nicks, Blunt Ends
- Clone into Blunt Expression Vector (3 Out-of-Frame Stop Codons)
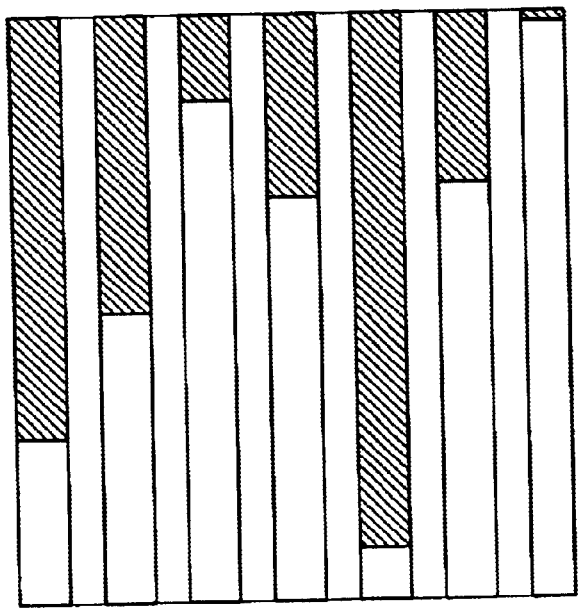
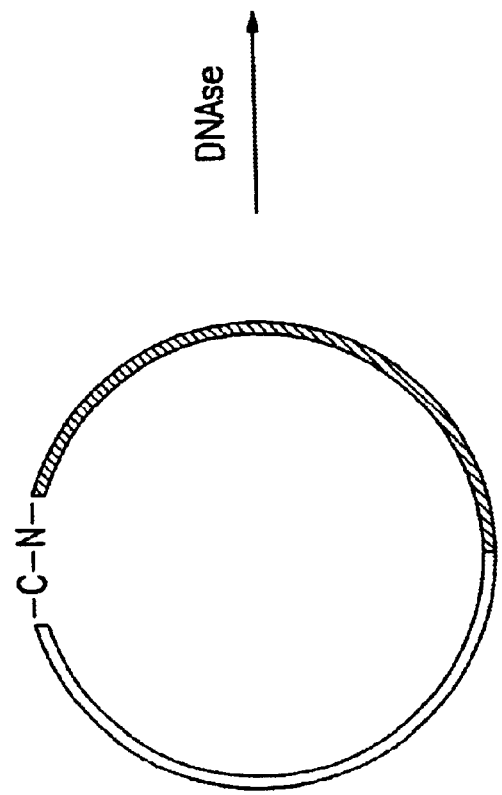
FIG. 6

US 6,699,687 B1

CIRCULARLY PERMUTED FLUORESCENT PROTEIN INDICATORS

This invention was made with Government support under Grant No. NS27177, awarded by the National Institutes of Health. The Government has certain rights in this invention.

TECHNICAL FIELD

The invention relates generally to fluorescent proteins and more particularly to compositions and methods for measuring the response of a sensor polypeptide to an environmental (e.g., biological, chemical, electrical or physiological) parameter.

BACKGROUND

Fluorescent $Ca^{2+}$ indicators such as fura-2, indo-1, fluo-3, and Calcium-Green have been the mainstay of intracellular $Ca^{2+}$ measurement and imaging (see, for example, U.S. Pat. No. 4,603,209 and U.S. Pat. No. 5,049,673). These relatively low molecular weight indicators can suffer from many technical problems relating to ester loading, leakage of the dyes from the cell, compartmentation in organelles, and perturbation of the indicators by cellular constituents. Although the $Ca^{2+}$-indicating photoprotein aequorin is targetable, the photoresponse to $Ca^{2+}$ is low since it is chemiluminescent. Moreover, aequorins need to incorporate exogenous coelenterazine.

Many effects of $Ca^{2+}$ in cells are mediated by $Ca^{2+}$ binding to calmodulin (CaM), which causes CaM to bind and activate target proteins or peptide sequences. Based on the NMR structure of CaM bound to the 26-residue M13 $Ca^{2+}$-binding peptide of myosin light-chain kinase, Porumb et al. fused the C-terminus of CaM via a Gly-Gly spacer to M13. $Ca^{2+}$ binding switches the resulting hybrid protein (CaM-M13) from a dumbbell-like extended form to a compact globular form similar to the CaM-M13 intermolecular complex (see, Porumb, T., et al., *Prot. Engineering* 7:109–115 (1994)).

Measurement of a binding member concentration in vitro or in vivo by non-invasive techniques can help elucidate the physiological function of the binding member. This can also aid in identifying changes that occur in a cell or organism in response to physiological stimuli. For example, cyclic AMP can be detected by fluorescence resonance energy transfer between separately labeled proteins that associate with each other but are not covalently attached to each other. See, U.S. Pat. No. 5,439,797.

The *Aequorea victoria* Green Fluorescent Protein (GFP) is useful as a marker for gene expression, as a fluorescent tag to aid in visualizing protein trafficking, and as a component of indicator systems that allow fluorescent sensing of small molecules and pH. Currently, GFPs use as a biosensor is limited to those systems that use GFP fusion proteins as partners for fluorescence resonance energy transfer (FRET) or those that use the subcellular redistribution of GFP fusion proteins as indicators of substrate concentration or the measurement of pH.

Currently, fluorescent molecules designed to measure interactions of proteins rely on cameleon molecules of tandem GFP constructs. In these constructs, conformational changes occur and alter the FRET between the GFPs and a ratiometric color change is noted. Such cameleon or FRET-sensitive constructs are large molecules in which protein conformation influences FRET efficiency of two GFPs of different colors. Although insertions into Green Fluorescent Protein have been attempted (see Abedi et al., *Nucleic Acids Research*, 26(2):623–630 (1998)) such insertions have been made to optimize the presentation of short peptide libraries and not to present binding molecules or sensor polypeptides. Additionally, such insertions have been only short insertions of about six amino acids in length. Until now, however, it has not been possible to make a single GFP molecules' fluorescence sensitive to a substrate other than hydrogen ions. There currently is a desire for smaller constructs useful in measuring interactions of molecules in vitro and in vivo.

SUMMARY

The inventors have discovered that when a sensor polypeptide is inserted into an Aequorea-related fluorescent protein (e.g., Green Fluorescent Protein (GFP), Yellow Fluorescent Protein (YFP) or Cyan Fluorescent Protein (CFP)) to form a construct, interaction of the sensor polypeptide with a biological, chemical, electrical or physiological parameter, for example, results in a change in fluorescence of the fluorescent protein. Such constructs are useful in measuring interactions of a sensor polypeptides with environmental stimuli in vitro or in vivo or in measuring particular characteristics of a cell (e.g., redox potential, intracellular ion concentration). These constructs rely on the responsiveness of a sensor polypeptide inserted within a GFP-sensor-related protein itself to influence the actual fluorescence of the fluorophore and not the interaction of tandem fluorescent molecules.

Accordingly, the present invention provides an isolated nucleic acid sequence which encodes a fluorescent indicator or chimeric construct, the indicator having a sensor polypeptide which is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide. The fluorescent protein moiety can be any fluorescent protein, for example, an Aequorea-related fluorescent protein moiety. More specifically, the Aequorea-related fluorescent protein can be, for example, a GFP, CFP or YFP moiety. The sensor polypeptide may be any polypeptide moiety, for example, a moiety that undergoes a conformational change upon interaction with a molecule, oxidation-reduction, or changes in electrical or chemical potential. The indicator may further include a linker moiety, linking the N- and C-termninal amino acids of the sensor polypeptide to the fluorescent protein. The linker may be any moiety that provides for linking of the sensor polypeptide to the fluorescent protein moiety such as for example, a nucleic acid that encodes GGTGEL (SEQ ID NO:1) or FKTRHN (SEQ ID NO:2). Two or more linker moieties may be attached to two separate polypeptides, that together form a sensor polypeptide. Additionally, the indicator may have a localization sequence, for localizing the indicator, for example, to a particular organelle of a cell. The sensor polypeptide or linker moiety may be inserted at numerous sites including, for example, one or more amino acids between residues 128–148, residues 155–160, residues 168–176 or residues 227–229 of the fluorescent protein moiety (e.g., GFP). More particularly Y145 is used for insertion of the linker or sensor polypeptide.

In another embodiment, the present invention provides a transgenic non-human animal having a nucleic acid sequence which encodes a fluorescent indicator or chimeric construct, the indicator having a sensor polypeptide which is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide.

In yet another embodiment, the present invention provides an expression vector having expression control sequences operatively linked to a nucleic acid sequence coding for the expression of a fluorescent indicator. The indicator having a sensor polypeptide which is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide.

In another embodiment, the present invention provides a host cell transfected with an expression vector having an expression control sequence operatively linked to a sequence coding for the expression of a fluorescent indicator. The host cell can be any host cell capable of transfection and expression of the indicator such as, for example, a prokaryote (e.g., E. coli), a eukaryotic cell (e.g., a yeast cell) or a mammalian cell.

In yet a further embodiment, the present invention provides a fluorescent indicator polypetide, the indicator having a sensor polypeptide which is responsive to a chemical, biological, electrical or physiological parameter, and a fluorescent protein moiety, wherein the sensor polypeptide is operatively inserted into the fluorescent protein moiety, and wherein the fluorscence of the fluorescent protein moiety is affected by the responsiveness of the sensor polypeptide.

In another embodiment, the present invention provides a fluorescent indicator or chimeric construct, the indicator having a sensor polypeptide which is responsive to a chemical, biological, electrical or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide the responsiveness resulting in protonation or deprotonation of the chromophore of the fluorescent protein moiety.

In yet another embodiment, the present invention provides a method for detecting the presence of a environmental parameter in a sample, by contacting the sample with a fluorescent indicator or chimeric construct, the indicator having a sensor polypeptide which is responsive to a chemical, biological, electrical, or physiological parameter, and a fluorescent protein moiety, wherein the sensor polypeptide is operatively inserted into the fluorescent protein moiety, and wherein the fluorescence of the fluorescent protein moiety is affected by the responsiveness of the sensor polypeptide, and detecting a change in fluorescence wherein a change is indicative of the presence of a parameter which affects the sensor polypeptide.

In another embodiment, the invention provides an isolated nucleic acid sequence encoding a circularly permuted fluorescent protein and the polypeptide encoded thereby, having a linker moiety linking the amino-termninal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein.

In another embodiment, the invention provides an expression vector comprising expression control sequences operatively linked to a nucleic acid sequence coding for the expression of a fluorescent indicator, the indicator having a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein. In a further embodiment, the invention provides a host cell containing the expression vector.

In yet another embodiment, the invention provides a method of producing a nucleic acid sequence encoding a fluorescent indicator, by linking a nucleic acid sequence encoding a linker moiety to the 5' nucleotide of a polynucleotide encoding a fluorescent protein, circularizing the polynucleotide with the nucleic acid sequence encoding the linker sequence, and cleaving the circularized polynucleotide with a nuclease, wherein cleavage linearizes the circularized polynucleotide.

In yet another embodiment, the invention provides a method of producing a circularly permuted fluorescent protein by expressing a nucleic acid sequence encoding a linker moiety linking the amino-terminal and carboxy-terminal amino acids of a fluorescent protein, wherein the amino and carboxy termini are linked as internal amino acids in the circularly permuted fluorescent protein moiety; and two terminal ends, wherein the first end is an amino-terminal end and the second end is a carboxy terminal end and wherein the amino and carboxy terminal ends of the circularly permuted fluorescent protein moiety are different from the amino-terminal and carboxy-terminal amino acids of the fluorescent protein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows the designs of a calmodulin or a Zif268 insertion into a fluorescent indicator of the present invention.

FIG. 2A shows pH effects on a calmodulin insertion indicator.

FIG. 2B shows titration curves for a calmodulin insertion indicator.

FIG. 6 shows the result of random digestion of a circularly permuted nucleic acid sequences.

DETAILED DESCRIPTION

Figure 3:
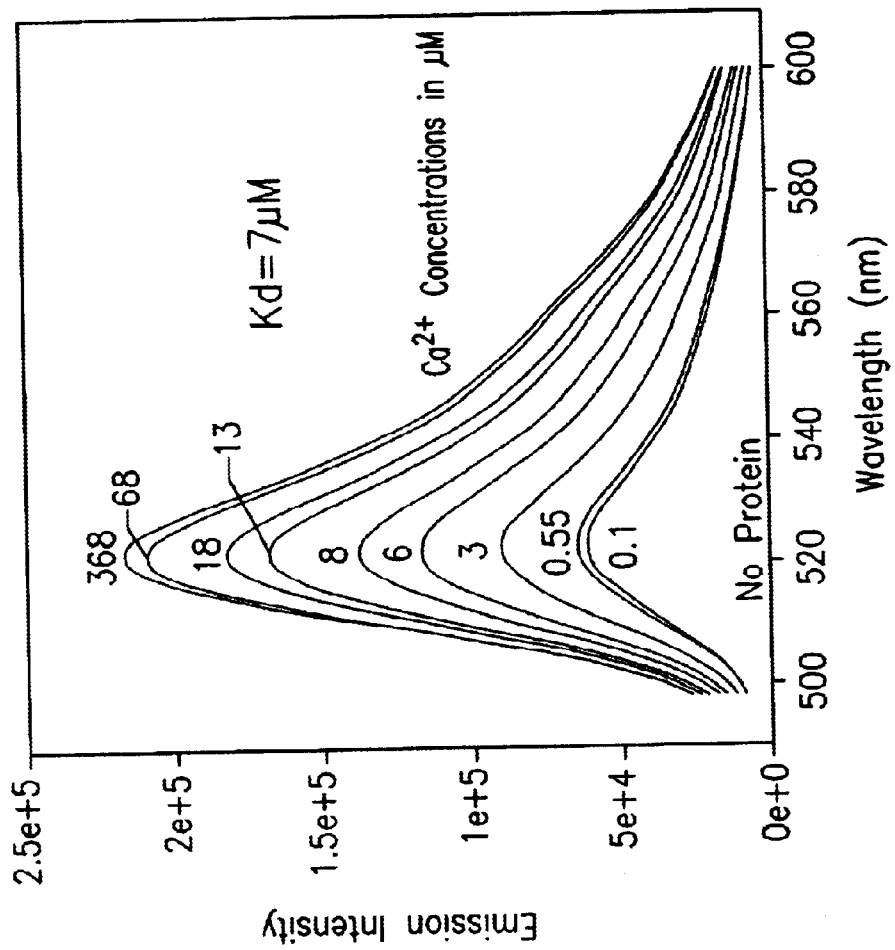
FIG. 3 further shows the effects of calcium concentration on fluorescence of a fluorescent indicator of the invention containing a sensor polypeptide of calmodulin.

The present invention relates to polynucleotides encoding fluorescent indicators, fluorescent indicators having a sensor polypeptide, and methods of producing and using the same.

The inventors have discovered a number of sites in Aequorea-related fluorescent protein moieties that are tolerant to insertions and rearrangements. The inventors have additionally discovered that the insertion of sensory polypeptides into such sites results in polypeptides that are useful in detection of chemical, biological, electrical or physiological parameters, for example. Such insertion sites include, for example, one-or more amino acids between residues 128–148, residues 155–160, residues 168–176 or residues 227–229 of the fluorescent protein moiety. Other positions which may tolerate insertions include, but are not limited to, residues 49–50, 78–79, 116–117, 134–135, 140–141, 157–158, 172–173, 194–195, 189–190 and 213–214 (see Abedi et al., *Nucleic Acids Research*, 26(2):623–630 (1998), the disclosure of which is incorporated herein). More specifically, the insertion is a Y145.

Additionally, the inventors have discovered that when a sensor polypeptide is inserted into an Aequorea-related fluorescent protein (e.g., GFP, YFP or CFP) that provides a response related to an interaction with a biological, chemical, electrical or physiological parameter, the responsiveness results in a change in fluorescence of the fluorescent protein. Such constructs are useful in measuring interactions of a sensor polypeptides with environmental stimuli in vitro or in vivo. These new constructs rely on, for example, detectable changes within a GFP-sensor-related protein itself to influence the actual fluorescence of the fluorophore and not the interaction of tandem fluorescent molecules. For example, when calmodulin is inserted into YFP at position Y145, interaction of calmodulin with its ligand (e.g., calcium) results in a change in the brightness of the fluorescent protein of between 2–8 fold.

The indicators of the present invention, are advantageous due to their reduced size as compared to the FRET-based sensors described above. The reduced size has importance in allowing the indicator to measure chemical, biological, electrical or physiological interactions with the sensor polypeptide in, for example, subcellular compartments previously inaccessible to the larger, FRET-based sensors. In addition, the maximal change in fluorescence intensity observed in the present indicators (e.g., up to 8 fold increase) are much larger than those in the cameleons (e.g., FRET-based sensors), which show only a 2 fold change in yellow to cyan intensity ratio.

Accordingly, the invention provides polynucleotides and nucleic acid sequences encoding fluorescent indicators having a fluorescent protein moiety and a sensor polypeptide, or fragments thereof, inserted in operable association into the fluorescent protein moiety, in which the sensor polypeptide is responsive to an environmental parameter (e.g., a chemical, a biological, a electrical, or a physiological parameter). Accordingly, the responsiveness of the sensor polypeptide causes a change in fluorescence of the fluorescent indicator. The degree of change in the fluorescence of the indicator is sensitive to pH.

As used herein, "operatively inserted" or "operably inserted" is meant between two amino acids of a polypeptide or two nucleotides of a nucleic acid sequence. Accordingly, insertion excludes ligating or attaching a polypeptide to the last terminal amino acid or nucleotide in a sequence.

As used herein, a "detectable change" or "responsiveness" means any response of a polypeptide to a chemical, biological, electrical, or physiological parameter or stimuli. A response includes small changes, for example, a shift in the orientation of an amino acid or peptide fragment of the sensor polypeptide as well as, for example, a change in the primary, secondary, or tertiary structure of a polypeptide, including for example, changes in protonation, electrical and chemical potential and or conformation. "Conformation" is the three-dimensional arrangement of the primary, secondary and tertiary structure of a molecule including side groups in the molecule; a change in conformation occurs when the three-dimensional structure of a molecule changes. Examples of conformational changes include a shift from α-helix to a β-sheet or a shift from β-sheet to a α-helix. It is understood that detectable changes need not be a conformational change, so long as the fluorescence of the fluorescent protein moiety is altered.

"Fragments" as used herein are a portion of a naturally occurring sensor protein which can exist in at least two different states or conformations. Fragments can have the same or substantially the same amino acid sequence as the naturally occurring protein. "Substantially the same" means that an amino acid sequence is largely, but not entirely, the same, but retains a functional activity of the sequence to which it is-related. In general two amino acid sequences are "substantially the same" or "substantially homologous" if they are at least 85% identical. Fragments which have different three dimensional structures as the naturally occurring protein are also included. The term "responsive" as used herein is intended to encompass any response of a polypeptide which is related to an interaction of a chemical, biological, electrical, or physiological parameter with a sensor polypeptide (e.g., conformational change in a voltage-gated ion channel (e.g., Shaker) in detection of membrane voltage across a biological membrane; phosphorylation of a hormone receptor resulting in a conformational change in the receptor upon hormone stimulation).

Example of sensor polypeptide useful in the present invention include calmodulin, a calmodulin-related protein moiety, recoverin, a nucleoside diphosphate or triphosphate binding protein, an inositol-1,4,5-triphosphate receptor, a cyclic nucleotide receptor, a nitric oxide receptor, a growth factor receptor, a hormone receptor, a ligand-binding domain of a hormone receptor, a steroid hormone receptor, a ligand binding domain of a steroid hormone receptor, a cytokine receptor, a growth factor receptor, a neurotransmitter receptor, a ligand-gated channel, a voltage-gated channel, a protein kinase C, a domain of protein kinase C, a cGMP-dependent protein kinase, an inositol polyphosphate receptor, a phosphate receptor, a carbohydrate receptor, an SH2 domain, an SH3 domain, a PTB domain, an antibody, an antigen-binding site from an antibody, a single-chain antibody, a zinc-finger domain, a protein kinase substrate, a protease substrate, a phosphorylation domain, a redox sensitive loop, a loop containing at least two cysteines that can form a cyclic disulfide, and a fluorescent protein moiety.

Where the fluorescent protein contains a second fluorescent protein and a sensor moiety within the insert, utilization of FRET based techniques to analyze or detect changes in chemical, biological or electrical parameters may be performed. For example, binding of an analyte such as calcium to a sensor polypeptide such as calmodulin would change the distance or angular orientation of the two fluorescent protein chromophores relative to each other and thereby modlulate FRET. A circularly permuted fluorescent protein may be tandemly or insertionally fused via a sensor moiety to a second fluorescent protein (which itself may optionally be a circular permutation) so that the FRET between the two fluorescent proteins changes in response to chemical, biological, or electrical parameters.

Classes of sensor polypeptides, which may be used in the compositions and methods of the invention include, but are not limited to, channel proteins, receptors, enzymes, and G-proteins.

Channel polypeptides useful with the invention include, but are not limited to voltage-gated ion channels including the potassium, sodium, chloride, G-protein-responsive, and calcium channels. A "channel polypeptide" is typically a polypeptide embedded in the cell membrane which is part of a structure that determines what particle sizes and or charges are allowed to diffuse into the cell. Channel polypeptides include the "voltage-gated ion channels", which are proteins imbedded in a cell membrane that serve as a crossing point for the regulated transfer of a specific ion or group of ions across the membrane. Specifically, Shaker potassium channels or dihydropuridine receptors from skeletal muscle may be advantageously used in the present invention. Several ion channel polypeptides of use with the invention are listed in Table 1.

TABLE 1

Ion Channels

| Gene Product | GenBank Accession No. |
| --- | --- |
| Human voltage-gated chloride ion channel CLCN5 | X91906 |
| Human delayed rectifier potassium channel (Isk) gene | L33815 |
| Human potassium channel protein (HPCN3) gene | M55515 |
| Human potassium channel (HPCN2) (mRNA) | M55514 |
| Human potassium channel (HPCN1) (mRNA) | M55513 |
| Human gamma subunit of epithelial amiloride-sensitive sodium channel (mRNA) | X87160 |
| Human beta subunit of epithelial amiloride-sensitive sodium channel | X87159 |

Channels also include those activated by intracellular signals such as those where the signal is by binding of ligand such as calcium, cyclic nucleotides, G-proteins, phosphoinositols, arachidonic acid, for example, and those where the signal is by a covalent modification such as phosphorylation, enzymatic cleavage, oxidation/reduction, and acetylation, for example. Channel proteins also include those activated by extracellular ligands (e.g., ionotropic receptors). These can be activated by acetylcholine, biogenic amines, amino acids, and ATP, for example.

A "receptor polypeptide" is a polypeptide found on a cell, often on a membrane, that can combine with a specific type of molecule, e.g., a ligand, which alters a function of the cell. Receptor polypeptides of use with the invention include, but are not limited to, the growth factor receptors, hormone receptors, cytokine receptors, chemokine receptors, neurotransmitter receptors, ligand-gated channels, and steroid receptors. Specifically polypeptides encoding insulin-like growth factor, insulin, somatostatin, glucagon, interleukins, e.g., IL-2, transforming growth factors (TGF-α, TGF-β), platelet-derived growth factor (PDGF), epidermal growth factor (EGF), nerve growth factor (NGF), fibroblast growth factor (FGF), interferon-γ (IFN-γ), and GM-CSF receptors are of use with the invention. Receptors such as those where binding of ligand is transmitted to a G-protein (e.g., for 7-transmembrane receptors) or kinase domains (for single transmembrane receptors) can be used with the invention. These can be activated by acetylcholine, biogenic amines, amino acids, ATP, and many peptides, such as opioids, hypothalamic-releasing hormones, neurohypophyseal hormones, pituitary hormones, tachykinins, secreting, insulins, somatostatins, and gastrointestinal peptides. Several receptor polypeptides of use with the invention are listed in Table 2.

TABLE 2

Receptors

| Gene Product | GenBank Accession No. |
| --- | --- |
| Human insulin receptor gene | M29929 |
| Human somatostatin receptor gene | L14856 |
| Human IL-2 receptor gene | X01057, X01058, XD1402 |
| Human TGF receptor (mRNA) | M8509 |
| Human PDGF receptor (mRNA) | M22734 |
| Human EGF receptor gene | X06370 |
| Human NGF receptor (mRNA) | M14764 |
| Human FGF receptor (mRNA) | M34641 |
| Human GM-CSF receptor (mRNA) | M73832 |
| Human IFN-y receptor (mRNA) | X62468 |

An "enzyme" is a polypeptide that acts as a catalyst, which speeds the rate at which biochemical reactions proceed do not alter the direction or nature of the reaction. Enzyme polypeptides useful in the invention include, but are not limited to, protein kinases, catalyses, amidase, phosphatases, guanylyl and adenylyl cyclases, and lipoxygenases. Polypeptides encoding the serine/threonine protein kinases are of use with the invention. Several genes encoding human enzymes of use with the invention are listed in Table 3.

TABLE 3

Enzymes

| Gene Product | GenBank Accession No. |
| --- | --- |
| Human cAMP dependent protein kinase AKAD 79 (mRNA) | M90359 |
| Human protein kinase C beta gene | D10022 |
| Human lipid-activate protein kinase PRK-1 (mRNA) | U33053 |
| Human guanine nucleotide binding protein alpha subunit gene | M21142, J03647, M21139 |
| Human serine/threonine kinase (mRNA) | M83780 |

The responsiveness of the sensor polypeptide (e.g., a change in conformation or state) that occurs in response to interaction of a sensor polypeptide with a chemical, biological, electrical or physiological parameter will, as discovered by the inventors, cause a change in fluorescence of the fluorescence indicator. The change can be the result of an alteration in the environment, structure, protonation or oligomerization status of the fluorescent indicator or chromophore. The molecular component responsible for a conformational change is known for many enzymes (e.g., Blostien, R., et al. (1997) *J. Biol. Chem.*, 272:24987–93; Shoelstein, Se. E., et al., (1993) *EMBO J.*, 12:795–802), receptors (e.g. Moyle, W. R., et al., (1995) *J. Biol. Chem.*, 270:20020–20031; Baron, V., et al., (1992), *J. Biol. Chem.* 267:23290–23294), and channels (e.g., Bouzat. A., et al., (1994) *Neuron*, 13: 1395–1402; Dulhanty, A. M., (1994) *Biochenmistry*, 33:4072–79) polypeptide. The optical properties (e.g., fluorescence) of the indicator which can be altered in response to the conformational change in the sensor polypeptide include, but are not limited to, changes in the excitation or emission spectrum, quantum yield, extinction coefficient, excited life-time and degree of self-quenching for example. The cause of the changes in these parameters may include but are not limited to changes in the environment, changes in the rotational or vibrational freedom of the sensor, changes in the angle of the sensor with respect to the exciting light or the optical detector apparatus, changes in the protonation or deprotonation of amino acids or side groups associated with a chromophore or changes in distance or dipole orientation between sensors on associated responsive polypeptides.

For example, insertion of a peptide or protein in place of tyrosine-145 (Y145) in mutants of GFP increases the sensitivity of fluorescence to quenching by acidic pH. When the inserted sensor polypeptide responds to a chemical, biological, electrical, or physiological parameter and undergoes a detectable change (e.g., a change in conformation), such interactions change the fluorescence via a shift in the acid sensitivity. For example, when calmodulin, a calcium sensing protein, replaces residue Y145 in a yellow mutant of GFP, calcium binding increases the fluorescence by up to 8-fold, depending on the pH at which the measurement is made. Other sites for insertion into GFP or GFP-mutants are allowable where circular permutation is tolerated, as discussed more fully below.

In the fluorescent indicator proteins of the invention, the sensor polypeptide is operably inserted into an optically active polypeptide (e.g., a fluorescent protein moiety). A protein-based "optically active polypeptide" is a polypeptide which contains a means for emitting light. Fluorescence is one optical property of an optically active polypeptide which can be used as the means of detecting the responsiveness of the sensor or responsive polypeptide of the fluorescent indicator or circularly permuted fluorescent proteins of the invention. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between the active and inactive states suffices for the utility of the fluorescent protein substrates of the invention in assays for activity. A measurable difference can be determined by determining the amount of any quantitative fluorescent property, e.g., the amount of fluorescence at a particular wavelength, or the integral of fluorescence over the emission spectrum. Optimally, the protein substrates are selected to have fluorescent properties that are easily distinguishable in the un-activated and activated conformational states.

One means of measuring fluorescence in a sample uses a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. For example, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. Other means of measuring fluorescence can also be used with the invention.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

Any fluorescent protein can be used in the invention, including proteins that fluoresce due to intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, a blue fluorescent protein ("BFP") is a protein that emits blue light, a yellow fluorescent protein ("YFP") is one that emits yellow light, and a cyan fluorescent protein ("CFP") is one that emits a greenish-blue light. GFPs have been isolated from the Pacific Northwest jellyfish, *Aequorea Victoria*, the sea pansy, *Renilla reniformis*, and *Phialidium gregariun*. See, Ward, W. W., et al., *Photochem. Photobiol.*, 35:803–808 (1982); and Levine, L. D., et al., *Comp. Biochem. Physiol.*, 72B:77–85 (1982).

A variety of Aequorea-related GFPs having useful excitation and emission spectra have been engineered by modifying the amino acid sequence of a naturally occurring GFP from *Aequorea Victoria*. (See, Prasher, D. C., et al., *Gene*, 111:229–233 (1992); Heim, R., et al., *Proc. Natl. Acad. Sci., USA*, 91:12501–04 (1994); U.S. Pat. No. 5,491,084; 5,625,048; International application PCT/US95/14692, filed Nov. 10, 1995). The cDNA of GFP can be concatenated with those encoding many other proteins; the resulting chimerics often are fluorescent and retain the biochemical features of the partner proteins. (See, Cubitt, A.B., et al., *Trends Biochem. Sci.* 20:448–455 (1995)). Mutagenesis studies have produced may GFP mutants, some having shifted wavelengths of excitation or emission (see, Heim, R. & Tsien, R. Y. *Current Biol.* 6:178–182 (1996)). Suitable pairs, for example a blue-shifted GFP mutant P4-3 (Y66H/Y145F) and an improved green mutant S65T can respectively serve as a donor and an acceptor for fluorescence resonance energy transfer (FRET). See, Tsien, R. Y., et al., *Trends Cell Biol.* 3:242–245 (1993). Such proteins are included in the invention sensor. A fluorescent protein is an "Aequorea-related fluorescent protein" if any contiguous sequence of 150 amino acids of the fluorescent protein has at least 85% sequence identity with an amino acid sequence, either contiguous or non-contiguous, from the wild type Aequorea green fluorescent protein. More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein. For example, where circularly permuted fluorescent proteins are concerned, any continuous sequence of the circularly permuted sequence which has identity to an Aequorea-related fluorescent protein, as described above, whether further N- or C-terminal than the comparison sequence is considered related. Similarly, the fluorescent protein can be related to Renilla or Phialidium wild-type fluorescent proteins using the same standards. Some Aequorea-related engineered versions described in Table 4. Other variants or mutants are within the scope of the invention as described, for example, in the Examples.

TABLE 4

| Clone | Mutation(s) | Excitation max (nm) | Emission max (nm) | Extinction Coefficient ($M^1cm^{-1}$) | Quantum yield |
|---|---|---|---|---|---|
| Wild type | none | 395 (475) | 508 | 21,000 (7,150) | 0.77 |
| P4 | Y66H | 383 | 447 | 13,500 | 0.21 |
| P4-3 | Y66H; Y145F | 381 | 445 | 14,000 | 0.38 |
| W7 | Y66W; N1461 M153T V163A N212K | 433 (453) | 475 (501) | 18,000 (17,100) | 0.67 |
| W2 | Y66W; I123V Y145H H148R M153T V163A N212K | 432 (453) | 480 | 10,000 (9,600) | 0.72 |
| S65T | S65T | 489 | 511 | 39,200 | 0.68 |
| P4-1 | S65T; M153A K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G;V68L S72A; T203Y | 513 | 527 | | |
| W1B | F64L;S65T Y66W; N1461 M153T V163A N212K | 432 (453) | 476 (503) | | |
| Emerald | S65T;S72A N149K M153T I167T | 487 | 508 | | |
| Sapphire | S72A;Y145F T2031 | 395 | 11 | | |

An additional clone, W1B1 included the following mutations: F64L; S65T; Y66W; F99S; and V163A.

Other fluorescent proteins can be used in the fluorescent indicators, such as, for example, yellow fluorescent protein from *Vibrio fischeri* strain Y-1, Peridinin-chlorophyll a binding protein from the dinoflagellate Symbiodinium sp. phycobiliproteins from marine cyanobacteria such as Synechococcus, e.g., phycoerythrin and phycocyanin, or oat phytochromes from oat reconstructed with phycoerythrobilin. These fluorescent proteins have been described in Baldwin, T. O., et al., *Biochemistry* 29:5509–5515 (1990), Morris, B. J., et al., *Plant Molecular Biology*, 24:673–677 (1994), and Wilbanks, S. M., et al., *J. Biol. Chem.* 268:1226–1235 (1993), and Li et al., *Biochemistry* 34:7923–7930 (1995), Murphy, J. T., & Lagarias, J. C., *Current Biology* 7:870–876 (1997).

The fluorescent indicators can be produced as chimeric proteins by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of CDNA from *A. Victoria* using primers based on the DNA sequence of *A. Victoria* green fluorescent protein. PCR methods are described in, for example, U.S. Pat. No. 4,683,195; Mullis, et al. *Cold Spring Harbor Symp. Quant. Biol.* 51:263 (1987), and Erlich, ed., *PCR Technology*, (Stockton Press, NY, 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In the chimeric proteins of the invention, the sensor polypeptide is operably inserted to an optically active polypeptide, which responds (e.g., a conformation change) to, for example, a cell signaling event. Cell signaling events that occur in vivo can be of very short duration. The optically active polypeptides of the invention allow measurement of the optical parameter, such as fluorescence, which is altered in response to the cell signal, over the same time period that the event actually occurs. Alternatively, the response can be measured after the event occurs (over a longer time period) as the response that occurs in an optically active polypeptide can be of a longer duration than the cell signaling event itself.

Nucleic Acid Constructs of the Invention

In another embodiment, the invention provides isolated nucleic acid sequences which encode fluorescent indicator polypeptides having operatively inserted therein a sensor polypeptide, or fragment thereof, which normally exists in one state e.g., conformational shape or charge, prior to an interaction with a chemical, biological, electrical or physiological parameter at which time it undergoes a response during or after the interaction of the chemical, biological, electrical or physiological parameter with the sensor polypeptide.

"Polynucleotide" or "nucleic acid sequence" refers to a polymeric form of nucleotides at least 10 bases in length. By "isolated nucleic acid sequence" is meant a polynucleotide that is no longer immediately contiguous with both of the coding sequences with which it was immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryotic or eukaryotic cell or organism, or which exists as a separate molecule (e.g. a cDNA) independent of other sequences. The nucleotides of the invention can be ribonucleotides, deoxyribonucleotides, or modified forms of either nucleotide. The term includes single and double stranded forms of DNA.

Nucleic acid sequences which encode a fluorescent indicator of the invention, wherein the indicator includes a sensor polypeptide, or fragment thereof, which normally has two or more states or conformational arrangements, and which undergoes a response during interaction with a chemical, biological, electrical or physiological parameter can be operatively linked to expression control sequences.

"Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and chimeric partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5 K promoter; CMV promoter) may be used. Promoters produced by recombinant DNA or synthetic techniques may also be used to provide for transcription of the nucleic acid sequences of the invention.

The term "fluorescent protein," and "fluorescent protein moiety" are used interchangeably and refer to any protein capable of emitting light when excited with appropriate electromagnetic radiation, and which has an amino acid sequence that is either natural or engineered and is derived from the amino acid sequence of an Aequorea-related fluorescent protein. The term "fluorescent indicator" refers to a fluorescent protein having a sensor polypeptide whose emitted light varies with the response state or conformation of the sensor polypeptide upon interaction with a chemical, biological, electrical or physiological parameter. The term also refers to a fluorescent protein whose amino acid sequence has been circularly permuted. The fluorescent indicators of the invention are also sensitive to pH in the range of about 5 to about 10. Thus, the invention provides, for example, a functional engineered fluorescent protein indicator whose amino acid sequence is substantially identical to the 238 amino acid Aequorea Victoria green fluorescence protein (SEQ ID NO:3).

The invention also includes functional polypeptide fragments of a fluorescent indicator. As used herein, the term "functional polypeptide fragment" refers to a polypeptide which possesses biological function or activity which is identified through a defined functional assay. The term "functional fragments of a functional engineered fluorescent protein" refers to fragments of a functional engineered protein that retain a function of the engineered fluorescent protein, e.g., the ability to fluoresce in manner which is dependent upon interactions of a chemical, biological, electrical or physiological parameter with a sensor polypeptide over the pH range 5 to 10.

Minor modifications of the functional engineered fluorescent indicator may result in proteins which have substantially equivalent activity as compared to the unmodified counterpart polypeptide as described herein. Such modifications may be deliberate, as by site-directed mutagenesis, or may be spontaneous. All of the polypeptides produced by these modifications are included herein as long as fluorescence of the engineered protein still exists.

By "substantially identical" or "substantially homologous" is meant a protein or polypeptide that retains the activity of a functional engineered fluorescent indicator, or nucleic acid sequence or polynucleotide encoding the same, and which exhibits at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. The reference amino acid sequence or nucleic acid sequence is considered homologous if the reference amino acid sequence is 80–95% homologous to any portion of the amino acid or nucleic acid sequence in question. For example, where a circularly permuted polypeptide sequence has been generated, the sequence will typically have an amino acid sequence wherein a carboxy terminal sequence is now more amino terminal than the original fluorescent protein. In such instances, the circularly permuted sequence is considered homologous because the carboxy terminal sequence is still present in the circularly permuted fluorescent protein even though it is now more N-terminal.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (e.g., assayed as described herein). Preferably, such a sequence is at least 85%, more preferably 90%, more preferably 95%, more preferably 98%, and most preferably 99% identical at the amino acid sequence to one of the sequences of EGFP (SEQ ID NO:4), EYFP (SEQ ID NO:5), ECFP (SEQ ID NO:7), EYFP-V68L/Q69K (SEQ ID NO:6), YFP H148G (SEQ ID NO:8), or YFP H148Q (SEQ ID NO:9). As discussed in the previous paragraph and more fully below, circularly permuted sequences fall within the definition of "substantially identical", for example if one or more amino acids of a circularly permuted polypeptide sequence is changed as described herein.

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

In some embodiments, the amino acid sequence of the protein includes one of the following sets of substitutions in the amino acid sequence of the Aequorea green fluorescent protein (SEQ ID NO:3): F64L/S65T/H231L, referred to herein as EGFP (SEQ ID NO:4); S65G/S72A/T203Y/H231L, referred to herein as EYFP (SEQ ID NO:5); S65G/V68L/Q69K/S72A/T203Y/H231L, referred to herein as EYFP-V68L/Q69K (SEQ ID NO:6); K26R/F64L/S65T/Y66W/N146I/M153T/V163A/N164H/H231L, referred to herein as ECFP (SEQ ID NO:7). The amino acid sequences of EGFP, EYFP, EYFP-V68L/Q69K, and ECFP are shown in Tables 5–8, respectively. The numbering of the amino acids conforms to that in native Aequorea GFP. Thus, the first serine is amino acid number 2 even if a valine (amino acid no. 1a) has been inserted to optimize ribosome initiation. Thus, F64L corresponds to a substitution of leucine for phenylalanine in the 64th amino acid following the initiating methionine.

TABLE 5

EGFP Amino Acid Sequence (SEQ ID NO:4)

MVSKGEELFTGVVPILVELDGDVNGHKFSVSGEGEGDATYGKLTLKFICTTGKLPVP
WPTLVTTLTYGVQCFSRYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRH
NIEDGSVQLADHYQQNTPIGDGPVLLPDNHYLSTQSALSKDPNEKRDHMVLLEFVTA
AGITLGMDELYK

TABLE 6

EYFP Amino Acid Sequence (SEQ ID NO:5)

MVSKGEELFTGVVPILVELDGDVNGHKFSVSGEGEGDATYGKLTLKFICTTGKLPVP
WPTLVTTFGYGVQCFARYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRH
NIEDGSVQLADHYQQNTPIGDGPVLLPDNHYLSYQSALSKDPNEKRDHMVLLEFVTA
AGITLGMDELYK

TABLE 7

EYFP-V68L/Q69K Amino Acid Sequence (SEQ ID NO:6)

MVSKGEELFTGVVPILVELDGDVNGHKFSVSGEGEGDATYGKLTLKFICTTGKLPVP
WPTLVTTFGYGLKCFARYPDHMKQHDFFKSAMPEGYVQERTIFFKDDGNYKTRAEV
KFEGDTLVNRIELKGIDFKEDGNILGHKLEYNYNSHNVYIMADKQKNGIKVNFKIRH
NIEDGSVQLADHYQQNTPIGDGPVLLPDNHYLSYQSALSKDPNEKRDHMVLLEFVTA
AGITLGMDELYK

TABLE 8

ECFP Amino Acid Sequence (SEQ ID NO:7)

MVSKGEELFTGVVPILVELDGDVNGHRFSVSGEGEGDATYGKLTLKFICTTGKLPVP
WPTLVTTLTWGVQCFSRYPDHMKQHDFFKSAMPEGYVQERTIFFKDDGNYKTRAEV
KFEGDTLVNRIELKGIDFKEDGNILGHKLEYNYISHNVYITADKQKNGIKAHFKIRHNI
EDGSVQLADHYQQNTPIGDGPVLLPDNHYLSTQSALSKDPNEKRDHMVLLEFVTAA
GITLGMDELYK

In other embodiments, the amino acid sequence of the protein is based on the sequence of the wild-type Aequorea green fluorescent protein (SEQ ID NO:3), but includes the substitution H148G or H148Q. In specific embodiments, these substitutions can be present along with other substitutions, e.g., the proteins can include the substitutions S65G/V68L/S72A/H148G/Q80R/T203Y (SEQ ID NO:8), which is referred to herein as the "YFP H148G mutant," S65G/V68L/S72A/H148Q/Q80R/T203Y, which is referred to herein as the "YFP L148Q mutant" (SEQ ID NO:9), the as well as EYFP-H148G (SEQ ID NO:10) and EFP-H 148Q (SEQ ID NO:11). The amino acid sequences of these mutants are shown in Tables 9–12, respectively.

chemically synthesizing the protein. Purity can be measured by any appropriate method, e.g., those described in column chromatography, polyacrylamide gel electrophoresis, or by HPLC analysis.

A protein or polypeptide is substantially free of naturally associated components when it is separated from those contaminants which accompany it in its natural state. Thus, a protein or polypeptide which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

TABLE 9

Amino Acid Sequence of YFP H148G (SEQ ID NO:8)

MSKGEELFTGVVPILVELDGDVNGHKFSVSGEGEGDATYGKLTLKFICTTGKLPVPWP
TLVTTFGYGLQCFARYPDHMKRHDFFKSAMPEGYVQERTIFFKDDGNYKTRAEVKFE
GDTLVNRIELKGIDFKEDGNILGHKLEYNYNSGNVYIMADKQKNGIKVNFKIRHNIED
GSVQLADHYQQNTPIGDGPVLLPDNHYLSYQSALSKDPNEKRDHMVLLEFVTAAGIT
HGMDELYK

TABLE 10

Amino Acid Sequence of YFP H148Q (SEQ ID NO:9)

MSKGEELFTGVVPILVELDGDVNGHKFSVSGEGEGDATYGKLTLKFICTTGKLPVPWP
TLVTTFGYGLQCFARYPDHMKRHDFFKSAMPEGYVQERTIFFKDDGNYKTRAEVKFE
GDTLVNRIELKGIDFKEDGNILGHKLEYNYNSQNVYIMADKQKNGIKVNFKIRHNIED
GSVQLADHYQQNTPIGDGPVLLPDNHYLSYQSALSKDPNEKRDHMVLLEFVTAAGIT
HGMDELYK

TABLE 11

Amino Acid Sequence of EYFP-H148G (SEQ ID NO:10)

MVSKGEELFTGVVPILVELDGDVNGHKFSVSGEGEGDATYGKLTLKFICTTGKLPVP
WPTLVTTFGYGVQCFARYPDHMKQHDFFKSAMPEGYVQERTIFFKDDGNYKTRAEV
KFEGDTLVNRIELKGIDFKEDGNILGHKLEYNYNSGNVYIMADKQKNGIKVNFKIRH
NIEDGSVQLADHYQQNTPIGDGPVLLPDNHYLSYQSALSKDPNEKRDHMVLLEFVTA
AGITLGMDELYK

TABLE 12

Amino acid Sequence of EYFP-H148Q (SEQ ID NO:11)

MVSKGEELFTGVVPILVELDGDVNGHKFSVSGEGEGDATYGKLTLKFICTTGKLPVP
WPTLVTTFGYGVQCFARYPDHMKQHDFFKSAMPEGYVQERTIFFKDDGNYKTRAEV
KFEGDTLVNRIELKGIDFKEDGNILGHKLEYNYNSQNVYIMADKQKNGIKVNFKIRH
NIEDGSVQLADHYQQNTPIGDGPVLLPDNHYLSYQSALSKDPNEKRDHMVLLEFVTA
AGITLGMDELYK

In some embodiments, the protein or polypeptide is substantially purified. By "substantially pure protein or polypeptide" is meant an functional engineered fluorescent polypeptide which has been separated from components which naturally accompany it. Typically, the protein or polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of the protein. A substantially pure protein may be obtained, for example, by extraction from a natural source (e.g., a plant cell); by expression of a recombinant nucleic acid encoding a functional engineered fluorescent protein; or by The invention also provides polynucleotides encoding the functional engineered fluorescent protein described herein. These polynucleotides include DNA, cDNA, and RNA sequences which encode functional engineered fluorescent proteins. It is understood that all polynucleotides encoding functional engineered fluorescent proteins are also included herein, as long as they encode a protein or polypeptide whose fluorescent emission intensity changes as pH varies between 5 and 10. Such polynucleotides include naturally occurring, synthetic, and intentionally manipulated polynucleotides. For example, the polynucleotide may be subjected to site-directed mutagenesis. The polynucleotides of the invention include sequences that are degenerate as a result of the genetic code. Therefore, all degenerate nucleotide sequences are included in the invention as long as the amino acid sequence of the functional engineered fluorescent protein or derivative is functionally unchanged.

Specifically disclosed herein is a polynucleotide sequence encoding a functional engineered fluorescent protein that includes one of the following sets of substitutions in the amino acid sequence of the Aequorea green fluorescent protein (SEQ ID NO:3): S65G/S72A/T203Y/H231L, S65G/V68L/Q69K/S72A/T203Y/H231L, or K26R/F64L/S65T/Y66W/N146I/M153T/V163A/N164H/H231L. In specific embodiments, the DNA sequences encoding EGFP, EYFP, ECFP, EYFP-V68L/Q69K, YFP H148G, and YFP H148Q are those shown in Table 13–20 (SEQ ID NOS:12 to 19), respectively.

The nucleic acid encoding functional engineered fluorescent proteins may be chosen to reflect the codon choice in the native *A. Victoria* coding sequence, or, alternatively, may be chosen to reflect the optimal codon frequencies used in the organism in which the proteins will be expressed. Thus, nucleic acids encoding a target functional engineered protein to be expressed in a human cell may have use a codon choice that is optimized for mammals, or especially humans.

TABLE 13

EGFP Nucleic Acid Sequence (SEQ ID NO:12)

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCG
CGCCGAGGTGAAGTTCGAGGGCGACACCCTGGTGAACCGCATCGAGCTGAAGGG
CATCGACTTCAAGGAGGACGGCAACATCCTGGGGCACAAGCTGGAGTACAACTAC
AACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTAC
CTGAGCACCCAGTCCGCCCTGAGCAAAGACCCCAACGAGAAGCGCGATCACATG
GTCCTGCTGGAGTTCGTGACCGCCGCCGGGATCACTCTCGGCATGGACGAGCTGT
ACAAGTAA

TABLE 14

EYFP Nucleic Acid Sequence (SEQ ID NO: 13)

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCTTCGGCTACGGCGTGCAGTGCTTCGCCC
GCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACA
ACAGCCACAACGTCTATATCATGGCCGACAAGCAGAAGAACGGCATCAAGGTGAA
CTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACC
TGAGCTACCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTAC
AAGTAA

TABLE 15

ECFP Nucleic Acid Sequence (SEQ ID NO: 14)

ATGGTGAGCAAGGGCGAGGAGCTGTTCACCGGGGTGGTGCCCATCCTGGTCGAGC
TGGACGGCGACGTAAACGGCCACAAGGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCCTGACCTGGGGCGTGCAGTGCTTCAGC
CGCTACCCCGACCACATGAAGCAGCACGACTTCTTCAAGTCCGCCATGCCCGAAG
GCTACGTCCAGGAGCGTACCATCTTCTTCAAGGACGACGGCAACTACAAGACCCG
CGCCGAGGTGAAGTTCGAGGGCGACACCCTGGTGAACCGCATCGAGCTGAAGGG
CATCGACTTCAAGGAGGACGGCAACATCCTGGGGCACAAGCTGGAGTACAACTAC
ATCAGCCACAACGTCTATATCACCGCCGACAAGCAGAAGAACGGCATCAAGGCCC
ACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTAC
CTGAGCACCCAGTCCGCCCTGAGCAAAGACCCCAACGAGAAGCGCGATCACATG
GTCCTGCTGGAGTTCGTGACCGCCGCCGGGATCACTCTCGGCATGGACGAGCTGT
ACAAGTAA

TABLE 16

EYFP-V68L/Q69K Nucleic Acid Sequence (SEQ ID NO: 15)

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCTTCGGCTACGGCCTGAAGTGCTTCGCCC
GCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACA
ACAGCCACAACGTCTATATCATGGCCGACAAGCAGAAGAACGGCATCAAGGTGAA
CTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACC
TGAGCTACCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTAC
AAGTAA

TABLE 17

Nucleotide Sequence of the YFP H148G Coding Region (SEQ ID NO: 16)

ATGAGTAAAGGAGAAGAACTTTTCACTGGAGTTGTCCCAATTCTTGTTGAATTAGA
TGGTGATGTTAATGGGCACAAATTTTCTGTCAGTGGAGAGGGTGAAGGTGATGCA
ACATACGGAAAACTTACCCTTAAATTTATTTGCACTACTGGAAAACTACCTGTTCCA
TGGCCAACACTTGTCACTACTTTCGGTTATGGTCTTCAATGCTTTGCAAGATACCCA
GATCATATGAAACGGCATGACTTTTTTCAAGAGTGCCATGCCCGAAGGTTATGTTCA
GGAAAGAACTATATTTTTCAAAGATGACGGGAACTACAAGACACGTGCTGAAGTC
AAGTTTGAAGGTGATACCCTTGTTAATAGAATCGAGTTAAAAGGTATTGATTTTAAA
GAAGATGGAAACATTCTTGGACACAAATTGGAATACAACTATAACTCAGGCAATGT
ATACATCATGGCAGACAAACAAAAGAATGGAATCAAAGTTAACTTCAAAATTAGA
CACAACATTGAAGATGGAAGCGTTCAACTAGCAGACCATTATCAACAAAATACTCC
AATTGGCGATGGCCCTGTCCTTTTACCAGACAACCATTACCTGTCCTATCAATCTGC
CCTTTCGAAAGATCCCAACGAAAAGAGAGACCACATGGTCCTTCTTGAGTTTGTA
ACAGCTGCTGGGATTACACATGGCATGGATGAACTATACAAA

TABLE 18

Nucleotide Sequence of the YFP H148Q Coding Region (SEQ ID NO: 17)

ATGAGTAAAGGAGAAGAACTTTTCACTGGAGTTGTCCCAATTCTTGTTGAATTAGA
TGGTGATGTTAATGGGCACAAATTTTCTGTCAGTGGAGAGGGTGAAGGTGATGCA
ACATACGGAAAACTTACCCTTAAATTTATTTGCACTACTGGAAAACTACCTGTTCCA
TGGCCAACACTTGTCACTACTTTCGGTTATGGTCTTCAATGCTTTGCAAGATACCCA
GATCATATGAAACGGCATGACTTTTTTCAAGAGTGCCATGCCCGAAGGTTATGTTCA
GGAAAGAACTATATTTTTCAAAGATGACGGGAACTACAAGACACGTGCTGAAGTC
AAGTTTGAAGGTGATACCCTTGTTAATAGAATCGAGTTAAAAGGTATTGATTTTAAA
GAAGATGGAAACATTCTTGGACACAAATTGGAATACAACTATAACTCACATAATGT
ATACATCATGGCAGACAAACAAAAGAATGGAATCAAAGTTAACTTCAAAATTAGA
CACAACATTGAAGATGGAAGCGTTCAACTAGCAGACCATTATCAACAAAATACTCC
AATTGGCGATGGCCCTGTCCTTTTACCAGACAACCATTACCTGTCCTATCAATCTGC
CCTTTCGAAAGATCCCAACGAAAAGAGAGACCACATGGTCCTTCTTGAGTTTGTA
ACAGCTGCTGGGATTACACATGGCATGGATGAACTATACAAA

TABLE 19

Nucleotide Sequence of tbe EYFP-H148G Coding Region (SEQ ID NO:18)

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCTTCGGCTACGGCGTGCAGTGCTTCGCCC
GCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACA
ACAGCGGCAACGTCTATATCATGGCCGACAAGCAGAAGAACGGCATCAAGGTGAA
CTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACC
TGAGCTACCAGTCCGCCCTGAGCAAAGACCCCAACGAGAAGCGCGATCACATGGT

TABLE 19-continued

Nucleotide Sequence of the EYFP-H148G Coding Region (SEQ ID NO:18)

CCTGCTGGAGTTCGTGACCGCCGCCGGGATCACTCTCGGCATGGACGAGCTGTAC
AAGTAA

TABLE 20

Nucleotide Sequence of the EYFP-H148Q Coding Region (SEQ ID NO:19)

ATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGCC
CGTGCCCTGGCCCACCCTCGTGACCACCTTCGGCTACGGCGTGCAGTGCTTCGCCC
GCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACA
ACAGCCAGAACGTCTATATCATGGCCGACAAGCAGAAGAACGGCATCAAGGTGAA
CTTCAAGATCCGCCACAACATCGAGGACGGCAGCGTGCAGCTCGCCGACCACTAC
CAGCAGAACACCCCCATCGGCGACGGCCCCGTGCTGCTGCCCGACAACCACTACC
TGAGCTACCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTAC
AAGTAA

The functional engineered fluorescent protein can also include a targeting sequence to direct the fluorescent protein to particular cellular sites by fusion to appropriate organellar targeting signals or localized host proteins. A polynucleotide encoding a targeting sequence can be ligated to the 5' terminus of a polynucleotide encoding the fluorescence such that the targeting peptide is located at the amino terminal end of the resulting fusion polynucleotide/polypeptide. The targeting sequence can be, e.g., a signal peptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties are known to those skilled in the art, or can be readily ascertained without undue experimentation.

In the present invention, the nucleic acid sequences encoding the fluorescent indicator or circularly permuted fluorescent protein of the invention may be inserted into a recombinant expression vector. The term "recombinant expression vector" refers to a plasmid, virus or other vehicle known in the art that has been manipulated by insertion or incorporation of the nucleic acid sequences encoding the chimeric peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector, or adeno or vaccinia viral vectors for expression in mammalian cells (Lee and Nathans, J. Biol. Chem., 263:3521, 1988), baculovirus-derived vectors for expression in insect cells, cauliflower mosaic virus, CaMV; tobacco mosaic virus, TMV.

The nucleic acid sequences encoding a fluorescent indicator or circularly permuted fluorescent protein of the invention can also include a localization sequence to direct the indicator to particular cellular sites by fusion to appropriate organellar targeting signals or localized host proteins. A polynucleotide encoding a localization sequence, or signal sequence, can be ligated or fused at the 5' terminus of a polynucleotide encoding the fluorescence indicator such that the signal peptide is located at the amino terminal end of the resulting chimeric polynucleotide/polypeptide. In the case of eukaryotes, the signal peptide is believed to function to transport the chimeric polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to those described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", Chapter 35 of Stryer, L., Biochemistry (4th ed.), W. H. Freeman, 1995. The localization sequence can also be a localized protein. Some important localization sequences include those targeting the nucleus (KKKRK; SEQ ID NO:20), mitochondrion (amino terminal MLRTSSLFTRRVQPSLFRNILRLQST; SEQ ID NO:21), endoplasmic reticulum (KDEL (SEQ ID NO:22) at C-terminus, assuming a signal sequence present at N-terminus), peroxisome (SKF at C-terminus), synapses (S/TDV or fusion to GAP 43, kinesin and tau) prenylation or insertion into plasma membrane (CaaX; SEQ ID NO:23, CC, CXC, or CCXX; SEQ ID NO:24, at C-terminus), cytoplasmic side of plasma membrane (chimeric to SNAP-25), or the Golgi apparatus (chimeric to furin). The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds.,.(Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Examples of agents which induce a sensor polypeptide, include agents that contain any of the amino acid sequences in Table 21, or a portion thereof with the proviso that the parameter must bind to a calmodulin sensor polypeptide. The parameter can be a subsequence of a calmodulin-binding domain. The moieties listed in Table 21 are recognized by the sensor polypeptide CaM. See, for example, Crivici, A. & Ikura, M. *Annu. Rev. Biophys. Biomol. Struct.* 24:84–116 (1995). The parameter can be modified to enhance the response of the fluorescent indicator to the parameter. Other parameter are known in the art for other sensor polypeptides.

interaction of the chemical, biological, electrical or physiological parameter with the sensor polypeptide. The linker moiety should be long enough and flexible enough to allow the sensor polypeptide to freely interact and respond to a particular parameter. The linker moiety is, preferably, a peptide moiety. The preferred linker moiety is a peptide between about one and 30 amino acid residues in length, preferably between about two and 15 amino acid residues. One preferred linker moiety is a -Gly-Gly- linker. The linker moiety can include flexible spacer amino acid sequences, such as those known in single-chain antibody research. For example, the linker moiety can be GGGGS $(GGGGS)_n$ (SEQ ID NO:56), GKSSGSGSESKS (SEQ ID NO:57), GSTSGSGKSSEGKG (SEQ ID NO:58), GSTSGSGKS-SEGSGSTKG (SEQ ID NO:59), GSTSGSGKSSEGKG, (SEQ ID NO:60) GSTSGSGKPGSGEGSTKG (SEQ ID NO:61), EGKSSGSGSESKEF (SEQ ID NO:62), GGTGEL (SEQ ID NO:1), FKTRHN (SEQ ID NO:2), or GGTGGS (SEQ ID NO:63). Linking moieties are described, for example, in Huston, J. S., et al., PNAS 85:5879–5883 (1988), Whitlow, M., et al., *Protein Engineering* 6:989–995 (1993), and Newton, D. L., et al., *Biochemistry* 35:545–553 (1996).

Depending on the vector utilized, any of a number of suitable transcription and translation elements, including

TABLE 21

| Target[a] | Sequence |
|---|---|
| skMLCK (M13) | KRRWKKNFIAVSAANRFKKISSSGAL (25*) |
| smMLCK (smMLCKp) | ARRKWQKTGHAVRAIGRLSS (26) |
| CaMKII | ARRKLKGAILTTMLATRNFS (27) |
| Caldesmon | GVRNIKSMWEKGNVFSS (28) |
| Calspermin | ARRKLKAAVKAVVASSRLGS (29) |
| PFK (M11) | FMNNWEVYKLLAHIRPPAPKSGSYTV (30) |
| Calcineurin | ARKEVIRNKIRAIGKMARVFSVLR (31) |
| PhK (PhK5) | LRRLIDAYAFRIYGHWVKKGQQQNRG (32) |
| (PhK13) | RGKFKVICLTVLASVRIYYQYRRVKPG (33) |
| $Ca^{2+}$-ATPase (C28W) | LRRGQILWFRGLNRIQTQIKVVNAFSSS (34) |
| 59-kDa PDE | RRKHLQRPIFRLRCLVKQLEK (35) |
| 60-kDa PDE | TEKMWQRLKGILRCLVKQLEK (36) |
| NOS (NO-30) | KRRAIGFKKLAEAVKFSAKLMGQ (37) |
| Type I AC (AC-28) | IKPAKRMKFKTVCYLLVQLMHCRKMFKA (38) |
| *Borderella periusssis* AC | IDLLWKIARAGARSAVGTEA (39) |
| Neuromodulin | KAHKAATKIQASFRGHITRKKLKGEKK (40) |
| Spectrin | KTASPWKSARLMVHTVATFNSIKE (41) |
| MARCKS | KKKKKRFSFKKSFKLSGFSFKKSKK (42) |
| F52 or MacMARKS | KKKKKFSFKKPFKLSGLSFKRNRK (43) |
| β-Adducin | KQQKEKTRWLNTPNTYLRVNVADEVQRNMGS (44) |
| HSP90a | KDQVANSAFQERLRKHGLEVI (45) |
| HIV-1 gp160 | YHRLRDLLLIVKRIVELLGRR (46) |
| BBMHBI | QQLATLIQKTYRGWRCRTHYQLM (47) |
| Dilute MHC | RAACIRIQKTIRGWLLRKRYLCMQ (48) |
| Mastoparan | INLKALAALAKKIL (49) |
| Melittin | GIGAVLKVLTTGLPALISWIKRKRQQ (50) |
| Glucagon | HSQGTFTTSDYSKYLDSRRAQDFVQWLMNT (51) |
| Secretin | HSDGTFTSELSRLRDSARLQRLLQGLV (52) |
| VIP | HSDAVFTDNYTRLRKQMAVKKYLNSILN (53) |
| GIP | YADGTFISDYSAIMNKIRQQDFVNWLLAQQQKS (54) |
| Model Peptide CBP2 | KLWKKLLKLLKKLLKLG (55) |

*- numbers in parentheses at end of sequences are SEQ ID NO:
[a]Abbreviations: AC, adenylyl cyclase; BBMHCI, brush-border myosin heavy chain-1; CaMKII, calmodulin kinase II; CBP2, calmodulin binding peptide-2; GIP, gastrin inhibitory peptide; HIV-1 gp160, human immunodeficiency virus envelope glycoprotein 160; HSP, heat-shock protein; MARCKS, myristoylated alaminte-rich C kinase substrate; MHC, myosin heavy chain; NOS, nitric oxide synthase; PDE, phosphodiesterase; PFK, phosphofructokinase; PhK, phosphorylase kinase; sk-, smMLCK, skeletal muscle- and smooth muscle-myosin light chain kinase; VIP, vasoactive intestinal peptide.

Where a linker moiety is present, the length of the linker moiety is chosen to optimize the kinetics and specificity of responsiveness of the sensor polypeptide induced by the constitutive and inducible promoters, transcription enhancer elements, transcription terminators, etc. may be used in the expression vector (see, e.g., Bitter, et al., Methods in Enzymology 153:516–544, 1987). These elements are well known to one of skill in the art.

In bacterial systems a number of expression vectors may be advantageously selected depending upon the intended use. For example, when large quantities of a protein of the invention is desired, vectors which direct the expression of high levels of chimeric protein products that are readily purified may be desirable. Those which are engineered to contain a cleavage site to aid in protein recovery are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516–544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

An alternative expression system which could be used to express the proteins of the invention is an insect system. In one such system, *Autographa californica* nuclear polyhedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051. Another alternative expression system includes plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent indicator or circularly permuted fluorescent protein.

By "transformation" is meant a permanent or transient genetic change induced in a cell following incorporation of new DNA (i.e. DNA exogenous to the cell). Where the cell is a mammalian cell, a permanent genetic change is generally achieved by introduction of the DNA into the genome of the cell.

By "transformed cell" is meant a cell into which (or into an ancestor of which has been introduced), by means of recombinant DNA techniques, a DNA molecule encoding a fluorescent indicator or circularly permuted fluorescent protein having an optically active polypeptide having operatively inserted therein a sensor polypeptide, or fragment thereof, which normally has two or more states, and which is affected by a chemical, biological, electrical or physiological parameter.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the chimeric polypeptide of the invention, and a second foreign DNA molecule encoding a selectable phenotype, such as the herpes simplex thymidine kinase gene. Another method is to use a eukaryotic viral vector, such as simian virus 40 (SV40) adenovirus, vaccinia virus, or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. Methods of stable transfer, meaning that the foreign DNA is continuously maintained in the host, are known in the art.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, secretion of the gene product should be used as host cells for the expression of fluorescent indicator. Such host cell lines may include but are not limited to CHO, VERO, BHK, HeLa, COS, MDCK, Jurkat, HEK-293, and W138.

Mammalian cell systems which utilize recombinant viruses or viral elements to direct expression may be engineered. For example, when using adenovirus expression vectors, the nucleic acid sequences encoding a fluorescent indicator or circularly permuted fluorescent protein of the invention may be ligated to an adenovirus transcription/translation control complex, e.g., the late promoter and tripartite leader sequence. This nucleic acid sequence may then be inserted in the adenovirus genome by in vitro or in vivo recombination. Insertion in a non-essential region of the viral genome (e.g., region El or E3) will result in a recombinant virus that is viable and capable of expressing the fluorescent indicator in infected hosts (e.g., see Logan & Shenk, *Proc. Natl. Acad. Sci. USA*, 81: 3655–3659, 1984). Alternatively, the vaccinia virus 7.5 K promoter may be used. (e.g., see, Mackett, et al., *Proc. Natl. Acad. Sci. USA*, 79: 7415–7419, 1982; Mackett, et al., *J. Virol.* 49: 857–864, 1984; Panicali, et al., *Proc. Natl. Acad. Sci. USA* 79: 4927–4931, 1982). Of particular interest are vectors based on bovine papilloma virus which have the ability to replicate as extrachromosomal elements (Sarver, et al., *Mol. Cell. Biol.* 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, *Proc. Natl. Acad. Sci. USA*, 81:6349–6353, 1984). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with the cDNA encoding a fluorescent indicator or circularly permuted fluorescent protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., Cell, 11: 223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA*, 77: 3567, 1980; O'Hare, et al., *Proc. Natl. Acad. Sci. USA*, 8:1527, 1981); gpt, which confers resistance to mycophenolic acid (Mulligan & Berg, *Proc. Natl. Acad. Sci. USA*, 78: 2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30: 147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA*, 85:8047, 1988); and ODC (ornithine decarboxylase) which confers resistance to the ornithine decarboxylase inhibitor, 2-(difluoro-methyl)-DL-ornithine, DFMO (McConlogue L., In: *Current Communications in Molecular Biology*, Cold Spring Harbor Laboratory, ed., 1987).

A fluorescent indicator or circularly permuted fluorescent protein of the invention can be produced by expression of nucleic acid encoding the protein in prokaryotes. These include but are not limited to microorganisms such as bacteria transformed with recombinant bacteriophage DNA, plasmid DNA or cosmid DNA expression vectors encoding a chimeric protein of the invention. A primary advantage of the optically active polypeptides of the invention is that they are prepared by normal protein biosynthesis, thus avoiding organic synthesis and the requirement for customized unnatural amino acid analogs. The constructs can be expressed in *E. coli* in large scale for in vitro assays. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. Alternatively, the substrates can be expressed directly in a desired host cell for assays in situ.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

It should be understood that a nucleic acid sequence can also function as the concentration or available parameter in another embodiment of the invention. For example, a response may result from the interaction of a nucleic acid sequence with a sensor polypeptide comprising a DNA binding protein motif.

Screening Assays

The invention features a method for determining the presence of a chemical, biological, electrical or physiological parameter, by contacting the sample with a fluorescent indicator or circularly permuted fluorescent protein of the invention; exciting the indicator or protein; and measuring the amount of an optical property of the indicator or protein in the presence and absence of a parameter, such that a change in the optical property is indicative of an affect of the parameter on the indicator or protein. A series of standards, with known levels of activity, can be used to generate a standard curve. The optical event, such as intensity of fluorescence, that occurs following exposure of the sample to the fluorescent indicator or protein is measured, and the amount of the optical property is then compared to the standard curve. A standard, with a known level of activity, can be used to generate a standard curve, or to provide reference standards. The optical event, such as fluorescence, that occurs following exposure of the sample to the fluorescent indicator or protein is measured, and the amount of the optical property (e.g., fluorescence) is then compared to the standard in order to generate a relative measure of the affect of the sample on the fluorescent indicator.

In another embodiment, the invention features a method for determining if a cell exhibits an activity, which includes transfecting the cell with a nucleic acid encoding a fluorescent indicator or circularly permuted fluorescent protein of the invention; exciting the fluorescent indicator or circularly permuted fluorescent protein; and measuring the amount of an optical property in the presence of the activity and in the absence of the activity, such that a change in the optical property is indicative of activity Typically, the optical property is calibrated against standard measurements to yield an absolute amount of protein activity.

The invention additionally, features methods for determining transient changes in a chemical, biological, electrical or physiological parameter, by contacting the sample with a fluorescent indicator or circularly permuted fluorescent protein of the invention and measuring a change in the optical property of the indicator over time.

It is understood that the cell containing a nucleic acid sequence encoding a fluorescent indicator or circularly permuted fluorescent protein of the invention can be used to co-transfect other genes of interest in order to determine the effect of the gene product of that gene on the cell or the sensor polypeptide of the fluorescent indicator or circularly permuted fluorescent protein. Therefore, a cell containing such a nucleic acid sequence is a composition provided by the present invention.

The invention can be used in screening assays to determine whether a compound (e.g., a drug, a chemical or a biologic) alters the activity of a particular protein, i.e., the sensor polypeptide (e.g., ligand binding to a receptor). In one embodiment, the assay is performed on a sample containing the chimeric protein in vitro. A sample containing a known amount of activity, such as an enzymatic activity, is mixed with a fluorescent indicator substrate of the invention, with the co-factors required for activity, and with a test compound. The amount of the enzyme activity in the sample is then determined by measuring the amount of an optical property, such as a fluorescent property, at least a first and second time after contact between the sample, the chimeric protein substrate of the invention, and any co-factors or components required to conduct the reaction, and the test compound. Then the amount of activity per mole of enzyme, for example, in the presence of the test compound is compared with the activity per mole of enzyme in the absence of the test compound. A difference indicates that the test compound alters the activity of the enzyme. In general a change in the optical parameter by any measurable amount between activity in the presence of the test compound as compared with the activity in the absence of the test compound, is indicative of activity.

In another embodiment, the ability of a compound to alter the activity of a particular protein (i.e., a sensor polypeptide) in vivo is determined. In an in vivo assay, cells transfected with a expression vector encoding a substrate of the invention are exposed to different amounts of the test compound, and the effect on the optical parameter, such as fluorescence, in each cell can be determined. Typically, the difference is calibrated against standard measurements to yield an absolute amount of protein activity. This provides a method for screening for compounds which affect cellular events (e.g., receptor-ligand binding, protein-protein interactions or protein kinase activation). In a given cell type, any measurable change between activity in the presence of the test compound as compared with the activity in the absence of the test compound, is indicative of activity.

The materials of the invention are ideally suited for a kit for determining the presence of an activity in a sample. Such a kit may contain a container containing a chimeric protein comprising an optically active polypeptide having operatively inserted therein a sensor polypeptide, or fragment thereof, which is affected by a change in a parameter or the environment, wherein optical properties of the sensor are altered in response to the change. In another embodiment, a kit of the invention contains an isolated nucleic acid sequence which encodes a chimeric protein comprising an optically active polypeptide having operatively inserted therein a sensor polypeptide, or fragment thereof, which is affected by a change in a parameter or the environment, wherein optical properties of the sensor are altered in response to the change. The nucleic acid sequence of the later kit may be contained in a host cell, preferably stably transfected. The cell could optionally be transiently transfected. Thus, the cell acts as an indicator kit in itself

Transgenic Animals

In another embodiment, the present invention relates to transgenic animals that have cells that express an optically active polypeptide having operatively inserted therein a sensor polypeptide, or fragment thereof, which normally is capable of existing in two or more states, and which causes a change in the optical properties of the optically active polypeptide upon environmental conditions or parameters. Transgenic animals expressing high levels of the tagged transgene may be obtained, for example, by over-expression of the transgene with an enhanced promoter and/or with high copy numbers of the transgene. The transgenic animal may be heterozygous or homozygous for an ablated or disrupted endogenous indicator gene.

The "non-human animals" of the invention comprise any non-human animal having nucleic acid sequence which encodes a fluorescent indicator or circularly permuted fluorescent protein of the invention. Such non-human animals include vertebrates such as rodents, non-human primates, sheep, dog, cow, pig, amphibians, reptiles and fish. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is-the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Viral infection can also be used to introduce transgene into a non-human animal (e.g., retroviral, adenoviral or any other RNA or DNA viral vectors). The developing non-human embryo can be cultured in vitro to the blastocyst stage. During this time, the blastomeres can be targets for retro viral infection (Jaenich, R., *Proc. Natl. Acad. Sci USA* 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J*. 6:383–388, 1987). Alternatively, infection can be perfon-ed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode the fluorescent indicator or circularly permuted fluorescent protein of the invention which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Methods for Identifying Insertion Sites

A number of methods for identifying insertion sites in fluorescent proteins, such as GFP, YFP and CFP are known in the art, including, for example, site directed mutagenesis, insertional mutagenesis, and deletional mutagenesis. Other methods, including that exemplified below and in the Examples, are known or easily ascertained by one skilled in the art (see, for example, Abedi et al., supra).

Sites in, for example, GFP mutants which can tolerate insertions of sensor polypeptides can be identified by generating mutant proteins by manipulating the DNA sequence such that a variety of different insertions are produced and screening the mutants by flow cytometry for mutants which retain fluorescence. Such insertions may include replacement of certain amino acids, as well as the addition of a new sequence without a corresponding deletion or replacement in the sequence of the fluorescent protein. Variants identified in this fashion reveal sites which can tolerate insertions while retaining fluorescence.

Additionally, circularly permutation techniques are also useful in identifying sites in fluorescent proteins which are capable of tolerating insertions while retain the ability to fluoresce. Such techniques include are exemplified herein as well as known to those of skill in the art (see, for example, Graf et al., *Proc. Natl. Acad. Sci USA*, 93:11591–11596 (October 1996), the disclosure of which is incorporated herein).

In circular permutations, the original N- and C-terminal amino acids of a fluorescent protein are engineered to be linked by a linker moiety. Such linker moieties include those described above, as well as other easily ascertain by one skilled in the art. This is typically performed at the nucleic acid level resulting in a polynucleotide sequence wherein the 5' codon encoding the N-terminal amino acid is linked to the 3' codon encoding the C-terminal amino acid, resulting in a circularized fluorescent protein nucleic acid sequence. The circularized sequence is then cleaved with a nuclease to create a linear polynucleotide sequence, the cleavage site corresponding to an amino acid in of the fluorescent protein. The cleavage of the circularized sequence is either random or specific depending on the desired product, nuclease, and desired sequence. The linearized polynucleotide, which contains sequence homologous to the starting fluorescent protein sequence, is cloned into an expression vector and expressed. The expressed polypeptide sequence is then screened, for example by flow cytometry, for polypeptides retaining the ability to fluoresce. Accordingly, polypeptides which retain the ability to fluorescence correspondingly, via identification of the cleavage site, identify amino acids which can tolerate insertions without destroying the ability of the fluorescent protein to fluoresce.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N. J., *Modern Molecular Photochemistry*, Menlo Park: Benjamin/ Cummings Publishing Col, Inc. (1978), pp. 296–361.

EXAMPLES

Cells and Protein Purification

Bacteria used in this study were BL21(DE3) Gold cells from Stratagene. Transformation was performed by electroporating cells suspended in 10% glycerol directly with a ligation mixture (0.1 cm cuvette, 12.5 kV/cm, 200Ω, 25 uFd). For protein expression, cells were grown in LB containing 100 mg/L Ampicillin to an $OD_{600}$ of 0.6, at which time they were induced with 1 mM Isopropylthiogalactoside. Bacteria were allowed to express recombinant protein for 6 hours at room temperature and then overnight at 4° C. The bacteria were then pelleted by centrifugation, resuspended in 50 mM Tris, 300 mM NaCl and lysed with a French Press. The bacterial lysates were centrifuged at 30,000×g for 30 minutes, and the supernatants were incubated with NiNTA resin (from Qiagen, used for purifying circularly permuted GFP and Calmodulin Insertions) or Cobalt Talon Resin (from Clontech, used for purifying zinc-finger inserts).

Cloning and Gene Construction

Yellow GFP mutants (YFPs) with peptide insertions replacing Y145 were made by performing two separate polymerase chain reactions (PCRs). The first PCR amplified the N terminal piece of YFP to include a 5' BamH1 site and 3' replacement of Y145 with the hexapeptide linker GGT-GEL (SEQ ID NO:1; coded for by DNA containing Kpn1 and Sac1 restriction sites for subsequent cloning). The second PCR amplified the C terminal piece of YFP to include the 5' linker (GGTGEL; SEQ ID NO:1) replacing Y145 and a 3' EcoR1 site. These two PCR products were combined, amplified with N and C terminal YFP primers to yield a full length cDNA containing the insertion. The full length cDNA was restricted with BamH1 and EcoR1, ligated and cloned into the BamH1 and EcoR1 sites of pRSET B (Invitrogen) to yield the plasmid pYFPins. Next, the cDNAs for Xenopus Calmodulin and the first zinc-finger motif from zif268 were amplified with PCR using primers containing 5' Kpn1 sites and 3' Sac1 sites and digested with Kpn1 and Sac1. Finally, insertions into YFPs were made by cloning cDNAs of inserted proteins in between the Kpn1 and Sac1 sites of pYFPins. (FIG. 1).

Protein Titrations

Protein pH titrations were carried out in 125 mM KCl, 20 mM NaCl, 0.5 mM $CaCl_2$, 0.5 mM $MgCl_2$, and 50 mM buffer. Buffers were chosen to span a wide pH range, and included citrate (pH4–5), MES (pH 5.5–6.5), HEPES (pH 7–8.15), glycine (pH 8.8–10.7), and phosphate (pH11.3–13.2). For each pH, a weakly buffered protein solution was mixed with an equal volume of the corresponding buffer solution and analyzed for total fluorescence in triplicate on a microplate fluorescence reader using a 482+/−10 nm excitation filter and a 532+/−14 nm emission filter. (FIG. 2A).

Calcium titrations of YFP-Calmodulin insertion proteins were done in a cuvette in a fluorescence spectrometer in 100 mM KCl, 10 mM MOPS at pH7.5 (buffer was run through a Chelex column to remove traces of calcium). Small aliquots of $CaCl_2$ were added to this cuvette and a full fluorescence emission spectrum was taken after each addition. (FIG. 2B, FIG. 3).

Figure 4:
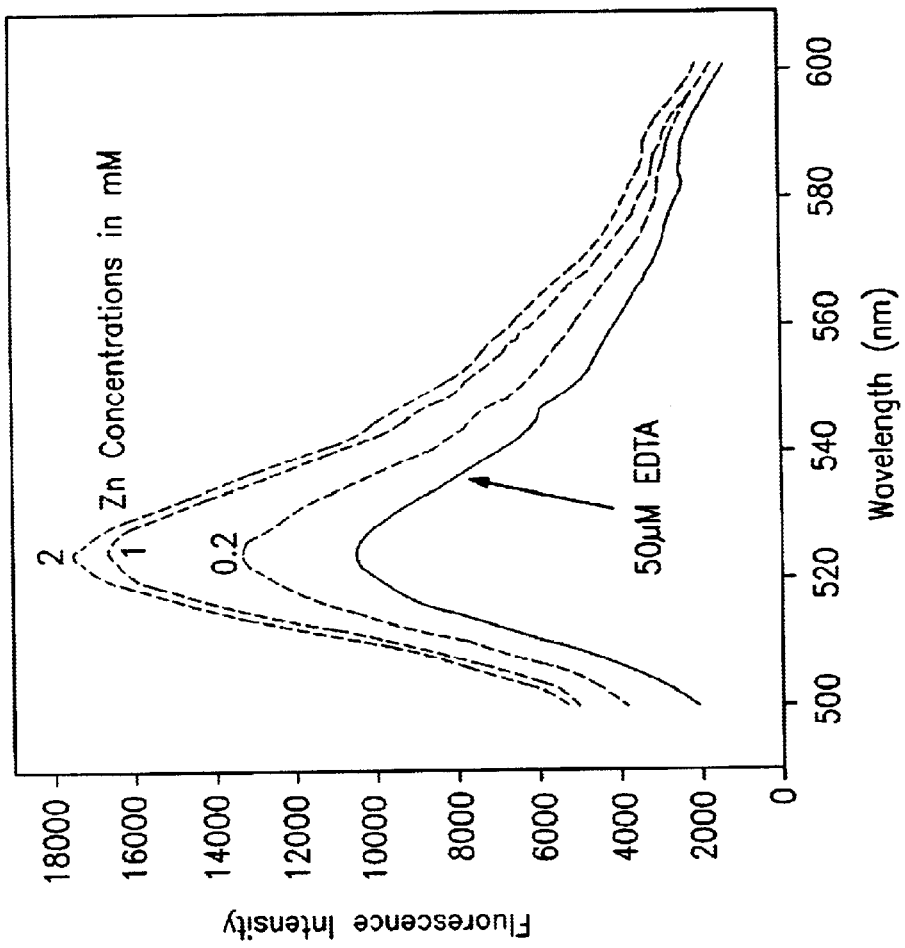
FIG. 4 show the effect of Zn concentration on fluorescence of a fluorescent indicator of the invention containing a sensor polypeptide of inserted Zif polypeptide.

Zinc titrations of YFP-zinc finger insertions were done in 50 mM MOPS, pH 7.0. A fluorescence emission spectrum was taken of the protein in buffer containing 50 uM EDTA, and then small aliquots of $ZnCl_2$ were added, and subsequent spectra were recorded. (FIG. 4).

Titration curves were generated by averaging the three intensity values for each pH (for microplate data) or be integrating the total emission intensity (for full spectra), plotting these data versus analyte concentration, and fitting a sigmoidal curve to the data.

YFP containing calmodulin replacing Y145 show an pH-sensitive increase in fluorescence intensity on calcium binding, with an apparent Kd of fluorescence of 7 $\mu$M. The increase in fluorescence observed at constant pH reflects a shift of 1 pKa unit between the calcium-free and calcium-bound states of the protein, as observed in pH titrations done in the presence of or absence of free calcium (FIG. 2). In addition, the absorbance of this protein changes from a predominantly ultraviolet, non-fluorescent band to a predominantly blue, fluorescent band on calcium binding at constant pH. Since other studies suggest that the non-fluorescent, ultraviolet-absorbing band represents the protonated chromophore and the fluorescent, blue-absorbing band represents the deprotonated chromophore, these data show that calcium, binding alters the equilibrium between protonated and deprotonated chromophore states, i.e. changes the pKa of fluorescence.

YFPs containing a zinc-finger motif derived from zif268 also increase in fluorescence on binding zinc. The change in fluorescence for Zn-sensing YFPs is substantially less than that of Calmodulin-YFPs described above. First, as Zn finger motifs contain cysteine residues in close proximity, they can be prone to oxidation, which would prevent zinc binding. Second, the change of inserted proteins on substrate binding is responsible for the change in pKa and therefore the change in fluorescence. It could be possible that zinc-finger motifs adopt a non-optimal conformation on binding zinc, leaving the chromophore still vulnerable to protonation. Last, each of the three reasons listed above concerning the performance of YFP-Calmodulin Insertions could in principle also apply analogously to the zinc finger insertions. As stated above, the zinc-finger inserted YFP reported here is just a first generation prototype of what will likely become a powerful new class of indicators.

Circular Permutations

Figure 5:
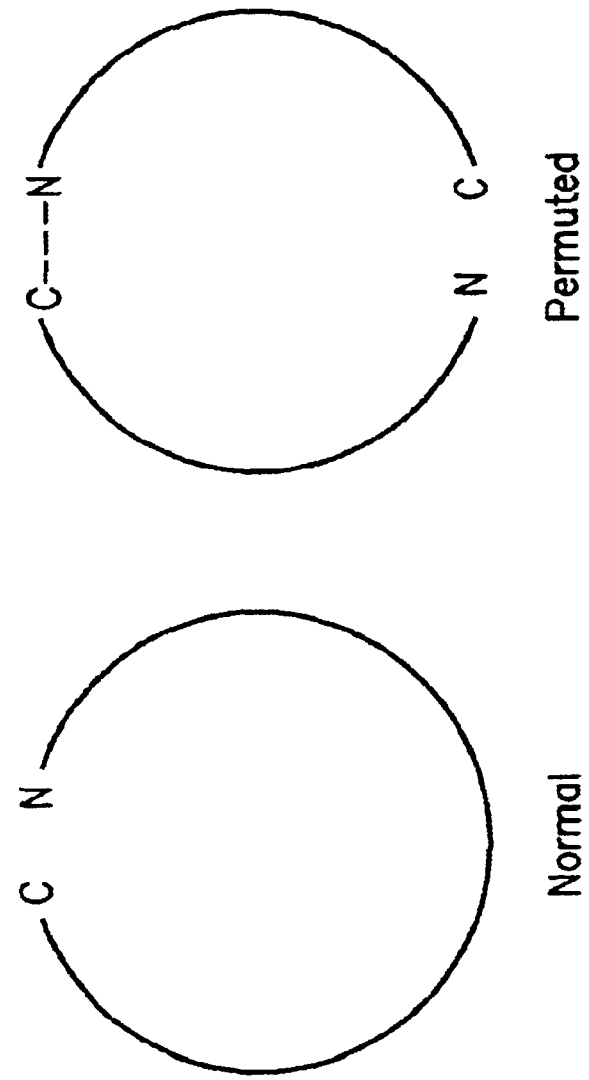
FIG. 5 shows the overall design of a circularly permuted polypeptide.

Circular Permutations of GFP mutants with a new N terminus at Y145 were made by performing two separate PCRs. The first PCR amplified the C terminal piece of a GFP mutant (N terminal in the final permuted gene) to have a 5' BamH1 site, the mutation Y145M, and a 3' hexapeptide linker (GGTGGS; SEQ ID NO:63) containing a Kpn1 site. The second PCR amplified the N terminal piece of the GFP mutant (C terminal in the final permuted gene) to have a 5' hexapeptide linker (GGTGGS; SEQ ID NO:63) containing a Kpn1 site, and a 3' EcoR1 site. The first PCR product was digested with sequentially with BamH1 and Kpn1, the second PCR product was digested sequentially with EcoR1 and Kpn1, and the fragments were purified by agarose gel electrophoresis. The N and C terminal PCR fragments were then cloned in a three part ligation into the BamH1/EcoR1 sites of pRSET B. (See FIG. 5).

To construct a cameleon molecule containing circularly permuted CFP instead of CFP (called YC3.2), the circularly permuted CFP cDNA was amplified with PCR to contain an 5' BamH1 site and a 3' Sac1 site, digested with BamH1 and Sac1 and agarose gel purified. Then, a plasmid consisting of the YC3.1 cDNA cloned into the BanH1 and EcoR1 sites of pRSET B was digested with BamH1 and Sac1, and the 4.2 kb DNA fragment (YC3.1D CFP) was agarose gel purified. The circularly permuted CFP cDNA was then ligated to the YC3.1 D CFP fragment, and the DNA was transformed into BL21 (DE3) Gold cells as described above.

Random Circular Permutations were based on the method of Graf, et al. with major modifications because their original conditions were found to be unsuccessful when applied to GFP cDNAs. Through extensive testing, it was found that circular permutation required 1) reducing the concentration of DNA used when circularizing the gene from 300 $\mu$g/mL to 5 $\mu$g/mL, 2) increasing the amount of DNAse used to relinearize the fragment from 1 U/mg DNA to 100 U/mg DNA, 3) changing the temperature of DNAse incubation from 16 degrees to 22 degrees Celsius, and switching the DNA repair enzyme used from T4 to T7 DNA polymerase. Accordingly, the method of Graf et al., was substantially modified as follows. An expression vector for the random circular permutations was made by ligating an oligonucleotide containing a 5' EcoRV site and three downstream stop codons in each reading frame between the BamH1 and EcoR1 sites of pRSET B. This vector ("pRSET triple stop") was digested with EcoRV, treated with Alkaline Phosphatase, and purified by agarose gel electrophoresis.

To make a library of circular permutations, the circularly permuted GFP gene described above was amplified by PCR with primers that created a final PCR amplicon starting and ending at an Xho1 site (ctcgag) coding for residues L141 and E142. The PCR product was digested with Xho1 and cloned into the Xho1 site of pBluescript. This plasmid was amplified in bacteria, purified with a Qiagen maxi-prep, digested with Xho1, and the ~730 bp fragment was agarose gel-purified to yield a linearized GFP gene. The linear fragment was circularized at a concentration of 5 μg/mL with 8000 U/mL T4 DNA ligase (New England Biolabs) overnight at 16° C. After ethanol precipitation, the DNA was digested with DNAse (100 U/mg DNA, Pharmacia) for 15 minutes at room temperature in 50 mM Tris HCl, pH7.5 and 1 mM $MnCl_2$. Digestion was stopped by phenol extraction, then subsequent phenol/chloroform/Isoamyl Alcohol and Chloroform/Isoamyl alcohol extractions. The DNA was ethanol precipitated, resuspended in 1×synthesis buffer (Stratagene) and incubated with T7 DNA polymerase (Stratagene) and T4 DNA ligase (Stratagene) at room temperature for 1 hour to repair DNA nicks and fill sticky ends. (FIG. 6).

The linear, repaired, randomly permuted DNA library was purified by agarose gel electrophoresis, ligated blunt into the pRSET triple stop expression vector, and electro-transformed into BL21 bacteria.

LB/agar plates containing ampicillin usually displayed a few thousand colonies per plate and were screened by digital imaging of fluorescence. The plates were illuminated with a 150 W xenon arc lamp through a 450–490 nm bandpass filter and a pair of fiber optic light guides (Oriel Instruments) positioned to illuminate the top surface of the agar as evenly as possible. The emitted fluorescence was selected by a 510–550 nm bandpass filter and focused by a f/1.2 camera lens (Nikon) onto a cooled charge-coupled-device camera (Photometrics). Digital images from the camera were analyzed with Metafluor software (Universal Imaging Corp.). Out of approximately 25,000 bacterial colonies screened, about 200 became fluorescent after 24 hours at 4° C., and 144 of these were picked for plasmid minipreps and restriction analysis. All plasmid minipreps were digested with HindIII and KpnI to analyze the site of permuted termini (HindIII cuts 3' to the GFP gene in pRSET B, Kpn1 cuts at the linker between N and C termini of GFP). Clones which gave restriction fragments of ~750 bp or no visible fragments from 100–1000 bp were considered to be regenerations of nearly wild-type sequence and were not investigated further. Clones which gave restriction fragments between 100 and 1000 bp but not 750 bp, were sequenced at their N and C termini to pinpoint the exact locations of new termini within the GFP sequence.

GFP forms a fluorescent circularly permuted protein when its native N and C termini are connected with the hexapeptide linker GGTGGS and new N termini are formed at E142, Y143, Y145, H148, D155, H169, E172, D173, A227, or I229 (See Table 22). The permuted protein with the N terminus at Y145 was made and studied for the Cyan, Green, and Yellow mutants of GFP (cpCFP, cpGFP, cpYFP). In each case, the protein had a higher pKa of fluorescence than its native counterpart, although the fluorescence spectra were similar. This suggests that interrupting GFP and its mutants at Y145 generally increases the chromophore's sensitivity to protonation, which is in agreement with the results obtained from the GFP insertions described above.

TABLE 22

Sequence Summary of Random Circular Permutations

| Starting Amino Acid | Ending Amino Acid* |
|---|---|
| E142M | NI44LSE |
| Y143N | NI46LSE |
| Y143I | NI44LSE |
| Y145I | N144 |
| H148I | N149LSE |
| H148I | K162SE |
| D155I | K156SE |
| H169H | N170LSE |
| H169I | N170LSE |
| E172M | I71DLSE |
| D173I | D173LSE |
| D173D | E172SE |
| A227A | A227I |
| I229I | I229I |

*"Starting Amino Acid" is the first amino acid for which is not coded for by the expression vector (which may also have been mutated), e.g. E142M means that the GFP starts at Position 142, but the glutamate residue has been changed to methionine by the cloning process. "Ending Amino Acid" is followed by the amino acid sequence added by the expression vector, e.g. N144LSE means that the GFP sequence ends with asparagine at position 144, but is appended by the C terminal tripeptide LSE. N144 meams that the protein simply ends with asparagine at position 144 with no addition peptide.

Figure 7:
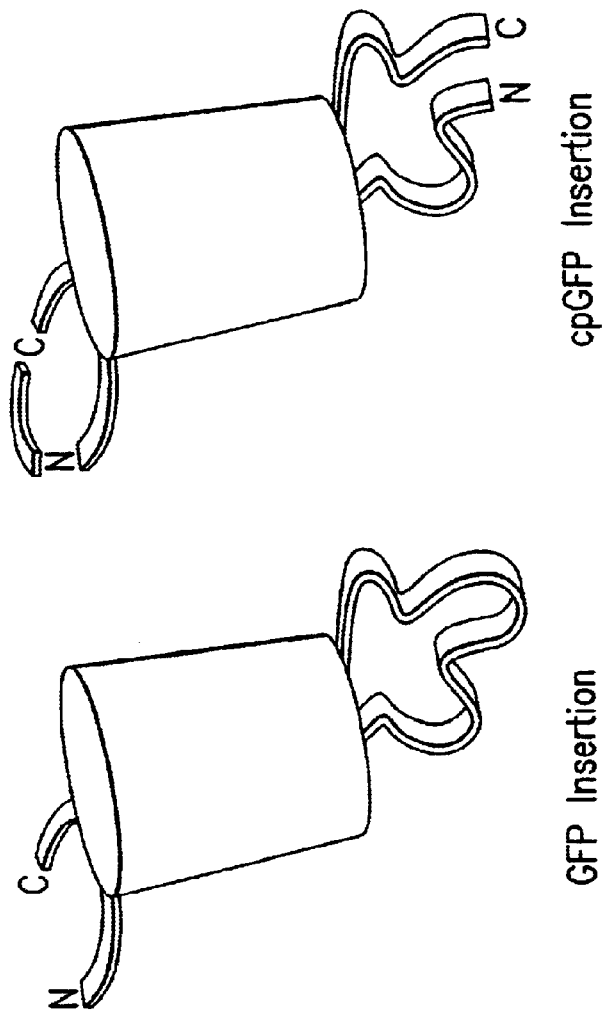
FIG. 7 shows insertions into GFP.
Figure 8:
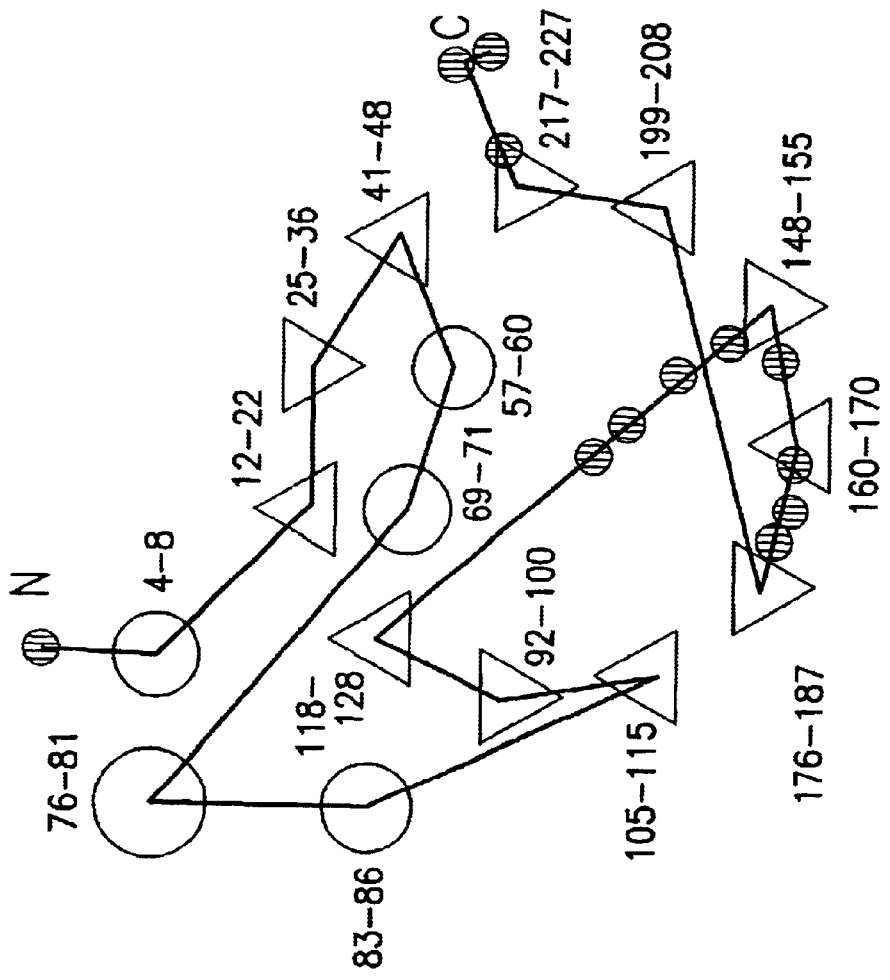
FIG. 8 shows a schematic diagram of potential insertional sites and sites for circular permutations in GFP.

To address cpCFP's orientation in space in fusion proteins, we constructed a cameleon molecule with cpCFP replacing CFP (YC3.2). With this modification, the FRET difference between calcium-free and calcium-bound states of cameleon changes dramatically compared to normal cameleons. This demonstrates that cpCFP maintains a different orientation in space than CFP, since other factors influencing FRET (inter-fluorophore distance and spectral overlap) have changed only very little. These data further suggest that the above list of possible cpGFP mutants represents a library of GFP mutants for use in FRET applications. Since most should have different orientations in space than regular GFP mutants, every FRET-based application of a GFP mutant that fails due to poor orientation could possibly be improved through use of cpGFP mutants. (FIG. 7).

One obvious use of cpGFP mutants relies purely on their increased pKas. Subcellular pH can be measured with appropriately targeted non-permuted GFP mutants; however, the dynamic range of pHs over which non-permuted GFPs can measure is limited by the pKas of available mutants. Since all circular permutants thus far investigated have higher pKas than their non-permuted counterparts, they theoretically extend the ability of GFPs to sense pH in more alkaline compartments, and could allow one to investigate relatively neutral compartments with blue-shifted mutants, which was previously not possible.

Another possible use of cpGFP mutants is in making novel insertions of GFP into other proteins for use as biosensors. GFP, because its termini are close in space, can be inserted into other proteins, but only rarely to date has it been shown to sense a conformational change in such a construct. When cpGFP mutants are inserted into a protein, they are topologically similar to the GFP insertion constructs described above, and they might reasonably be expected to have similar sensing properties as GFP insertions. (FIG. 7).

GFP mutants with peptide insertions replacing Y145 were made by performing two separate polymerase chain reactions (PCRs). The first PCR amplified the N-terminal piece of GFP to include a 5' BAMH1 site and 3' replacement of Y145 wit the hexapeptide linker GGTGEL (SEQ ID NO:1; coded for by DNA containing KpnI and SacI restriction sites for subsequent cloning). The second PCR amplified the C-terminal piece of GFP to include the 5' linker (GGTGEL; SEQ ID NO: 1) replacing Y145 and a 3' EcoR1 site. These two PCR products were combined, amplified with N- and C-terminal GFP primers to yield a full length fragment, restricted with BamH1 and EcoR1, ligated and cloned into the BamH1 and EcoR1 sites of pRSET B (Invitrogen). Subsequent insertions into this GFP were made by cloning nucleic acid sequences of a desired binding moiety in between the KpnI and SadI sites of this plasmid. Any sensor polypeptide can be inserted into a fluorescence protein (e.g., GFP, YFP, or CFP) by analogy to the method described above and put in a cell by introducing the cDNA coding for the protein into the cell in a vector that directs protein production. The indicator is then visualized using a fluorescence.

A number of embodiments of the present invention have been described. Nevertheless, it will be understood that various modifications may be made without departing from the spirit and scope of the invention. Accordingly, other embodiments are within the scope of the following claims.

What is claimed is:

1. An isolated nucleic acid sequence encoding a circularly permuted Aequorea-related fluorescent protein moiety which provides measurable fluorescence in a fluorescence screening assay, comprising:
   a linker moiety linking the amino-termninal and carboxy-terminal amino acids of a fluorescent protein, wherein the amino and carboxy termini are linked as internal amino acids in the circularly permuted fluorescent protein moiety; and
   two terminal ends, wherein the first end is an amino-terminal end and the second end is a carboxy terminal end, wherein the amino and carboxy terminal ends of the circularly permuted fluorescent protein moiety are different from the amino-terminal and carboxy-terminal amino acids of the fluorescent protein, wherein amino acid residues of said fluorescent protein are numbered in conformance with native Aequorea green fluorescent protein (SEQ ID NO:3) and wherein the first serine residue following methionine-1 in said fluorescent protein is designated amino acid residue 2, and wherein the amino-terminal end is selected from the group consisting E142, Y143, Y145, H148, D155, H169, E172, D173, A227 and I229, and the carboxy-terminal end is selected from the group consisting of N144, N146, N144, N149, K162, K156, N170, I171, D173, E172, A227, and I229, of the fluorescent protein, respectively.

2. The nucleic acid sequence of claim 1, wherein the Aequorea-related protein moiety is a green fluorescent protein (GFP), a cyan fluorescent protein (CFP) or a yellow fluorescent protein (YFP).

3. The nucleic acid sequence of claim 1, wherein the linker moiety encodes GGTGEL (SEQ ID NO:1), GGTGGS (SEQ ID NO:63) or FKTRHN (SEQ ID NO:2).

4. The nucleic acid sequence of claim 1, wherein the amino-terminal end or the carboxy terminal end of the indicator has an amino acid residue corresponding to any of residues 128–148, residues 155–160, residues 168–176 or residues 227–229 of the fluorescent protein.

5. The nucleic acid of claim 1, further comprising a polynucleotide encoding a sensor polypeptide selected from the group consisting of calmodulin, a calmodulin binding fragment, and a calmodulin-related protein.

6. The nucleic acid of claim 5, wherein the sensor polypeptide changes conformation upon interaction with a response-inducing member.

7. The nucleic acid of claim 5, wherein the sensor polypeptide is calmodulin or a calmodulin-related protein moiety.

8. The nucleic acid of claim 5, wherein the sensor polypeptide is selected from the group consisting of a calmodulin-binding domain of skMLCKp, smMLCK, CaMKII, Caldesmon, Calspermin, phosphofructokinase calcineurin, phosphorylase kinase, Ca2+-ATPase 59 kDa PDE, 60 kDa PDE, nitric oxide synthase, type I adenylyl cyclase, *Bordetella pertussis* adenylyl cyclase, Neuromodulin, Spectrin, MARCKS, F52, β-Adducin, HSP90a, HIV-1 gp160, BBMHBI, Dilute MHC, Mastoparan, Melittin, Glucagon, Secretin, VIP, GIP, and Model Peptide CBP2.

9. The nucleic acid of claim 1, wherein the circularly permuted fluorescent protein further comprises a localization sequence.

10. An expression vector containing the nucleic acid sequence of claim 1.

11. An expression vector comprising expression control sequences operatively linked to a nucleic acid sequence coding for the expression of a circularly permuted Aequorea-related fluorescent protein moiety which provides measurable fluorescence in a fluorescence screening assay, comprising:
   a linker moiety linking the amino-terminal and carboxy-termninal amino acids of a fluorescent protein, wherein the amino and carboxy termini are linked as internal amino acids in the circularly permuted fluorescent protein moiety; and
   two terminal ends, wherein the first end is an amino-terminal end and the second end is a carboxy terminal end, wherein the amino and carboxy terminal ends of the circularly permuted fluorescent protein moiety are different from the amino-terminal and carboxy-terminal amino acids of the fluorescent protein, wherein amino acid residues of said fluorescent protein are numbered in conformance with native Aequorea green fluorescent protein (SEQ ID NO:3) and wherein the first serine residue following methionine-1 in said fluorescent protein is designated amino acid residue 2, and wherein the amino-terminal end is selected from the group consisting E142, Y143, Y145, H148, D155, H169, E172, D173, A227 and I229, and the termninal end is selected from the group consisting of N144, N146, N144, N149, K162, K156, N170, I1171, D173, E172, A227, and I229, of the fluorescent protein, respectively.

12. A host cell transfected with an expression vector comprising an expression control sequence operatively linked to a nucleic acid sequence coding for the expression of a circularly permuted Aequorea-related fluorescent protein moiety which provides measurable fluorescence in a fluorescence screening assay, comprising:
   a linker moiety linking the amino-terminal and carboxy-terminal amino acids of a fluorescent protein, wherein the amino and carboxy termini are linked as internal amino acids in the circularly permuted fluorescent protein moiety; and
   two terminal ends, wherein the first end is an amino-terminal end and the second end is a carboxy terminal end, wherein the amino and carboxy terminal ends of the circularly permuted fluorescent protein moiety are different from the amino-terminal and carboxy-terminal amino acids of the fluorescent protein, wherein amino acid residues of said fluorescent protein are numbered in conformance with native Aequorea green fluorescent protein (SEQ ID NO:3) and wherein the first serine residue following methionine-1 in said fluorescent protein is designated amino acid residue 2, and wherein the amino-terminal end is selected from the group consisting E142, Y143, Y145, H148. D155, H169, E172, D173, A227 and I129, and the carboxy-terminal end is selected from the group consisting of N144, N146, N144, N149, K162, K156, N170, I171, D173, E172, A227, and I129, of the fluorescent protein, respectively.

13. The cell of claim 12, wherein the cell is a prokaryote.

14. The cell of claim 13, wherein the cell is *E. coli*.

15. The cell of claim 12, wherein the cell is a eukaryotic cell.

16. The cell of claim 15, wherein the cell is a yeast cell.

17. The cell of claim 15, wherein the cell is a mammalian cell.

18. A method of producing a nucleic acid sequence coding for the expression of a circularly permuted fluorescent Aequorea-related protein which provides measurable fluorescence in a fluorescence screening assay, comprising:
   linking a nucleic acid sequence encoding a linker moiety to the 5' nucleotide of a polynucleotide encoding a fluorescent protein, wherein amino acid residues of said fluorescent protein are numbered in conformance with native Aequorea green fluorescent protein (SEQ ID NO:3), wherein the first serine residue following methionine-1 in said fluorescent protein is designated amino acid residue 2, and wherein the amino-terminal end is selected from the group consisting E142, Y143, Y145, H148, D155, H169, E172, D173, A227 and I129, and the c terminal end is selected from the group consisting of N144, N146, N144, N149, K162, K156, N170, I171, D173, E172, A227, and I129, of the fluorescent protein, respectively;
   circularizing the polynucleotide with the nucleic acid sequence encoding the linker sequence; and
   cleaving the circularized polynucleotide with a nuclease, wherein cleavage linearizes the circularized polynucleotide.

19. A method of producing a circularly permuted fluorescent protein comprising expressing the nucleic acid sequence produced by the method of claim 18.

* * * * *

SEQUENCE LISTING

```
<160> NUMBER OF SEQ ID NOS: 63

<210> SEQ ID NO 1
<211> LENGTH: 6
<212> TYPE: PRT
<213> ORGANISM: Artificial Sequence
<220> FEATURE:
<223> OTHER INFORMATION: Linker moiety

<400> SEQUENCE: 1

Gly Gly Thr Gly Glu Leu
 1               5

<210> SEQ ID NO 2
<211> LENGTH: 6
<212> TYPE: PRT
<213> ORGANISM: Artificial Sequence
<220> FEATURE:
<223> OTHER INFORMATION: Linker moiety

<400> SEQUENCE: 2

Phe Lys Thr Arg His Asn
 1               5

<210> SEQ ID NO 3
<211> LENGTH: 238
<212> TYPE: PRT
<213> ORGANISM: Aequorea victoria

<400> SEQUENCE: 3

Met Ser Lys Gly Glu Glu Leu Phe Thr Gly Val Val Pro Ile Leu Val
 1               5                  10                  15

Glu Leu Asp Gly Asp Val Asn Gly Gln Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
```

```
              115                 120                 125
Asp Phe Lys Glu Asp Gly Asn Ile Leu Gly His Lys Met Glu Tyr Asn
            130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Ile Leu Leu Glu Phe Val
210                 215                 220

Thr Ala Ala Gly Ile Thr His Gly Met Asp Glu Leu Tyr Lys
225                 230                 235
```

<210> SEQ ID NO 4
<211> LENGTH: 239
<212> TYPE: PRT
<213> ORGANISM: Aequorea victoria

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 5
<211> LENGTH: 239

<212> TYPE: PRT
<213> ORGANISM: Aequorea victoria

<400> SEQUENCE: 5

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 6
<211> LENGTH: 239
<212> TYPE: PRT
<213> ORGANISM: Aequorea victoria

<400> SEQUENCE: 6

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Phe Gly Tyr Gly Leu Lys Cys Phe Ala Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 7
<211> LENGTH: 239
<212> TYPE: PRT
<213> ORGANISM: Aequorea victoria

<400> SEQUENCE: 7

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 8

-continued

```
<211> LENGTH: 238
<212> TYPE: PRT
<213> ORGANISM: Aequorea victoria

<400> SEQUENCE: 8

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser Gly Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 9
<211> LENGTH: 238
<212> TYPE: PRT
<213> ORGANISM: Aequorea victoria

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
    130                 135                 140

Tyr Asn Ser Gln Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235

<210> SEQ ID NO 10
<211> LENGTH: 239
<212> TYPE: PRT
<213> ORGANISM: Aequorea victoria

<400> SEQUENCE: 10

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser Gly Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 11
<211> LENGTH: 239
<212> TYPE: PRT
<213> ORGANISM: Aequorea victoria

<400> SEQUENCE: 11

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser Gln Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 12
<211> LENGTH: 720
<212> TYPE: DNA
<213> ORGANISM: Aequorea victoria

<400> SEQUENCE: 12
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600

-continued

```
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 13
<211> LENGTH: 720
<212> TYPE: DNA
<213> ORGANISM: Aequorea victoria

<400> SEQUENCE: 13

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcggcta cggcgtgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 14
<211> LENGTH: 720
<212> TYPE: DNA
<213> ORGANISM: Aequorea victoria

<400> SEQUENCE: 14

```
atggtgagca agggcgagga gctgttcacc ggggtggtgc ccatcctggt cgagctggac     60
ggcgacgtaa acggccacag gttcagcgtg tccggcgagg gcgagggcga tgccacctac    120
ggcaagctga ccctgaagtt catctgcacc accggcaagc tgcccgtgcc ctggcccacc    180
ctcgtgacca ccctgacctg gggcgtgcag tgcttcagcc gctaccccga ccacatgaag    240
cagcacgact tcttcaagtc cgccatgccc gaaggctacg tccaggagcg taccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg cccacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 15
<211> LENGTH: 720
<212> TYPE: DNA
<213> ORGANISM: Aequorea victoria

<400> SEQUENCE: 15

```
atggtgagca agggcgagga gctgttcacc ggggtggtgc ccatcctggt cgagctggac     60
```

-continued

| | |
|---|---|
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgaag tgcttcgccc gctacccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 16
<211> LENGTH: 714
<212> TYPE: DNA
<213> ORGANISM: Aequorea victoria

<400> SEQUENCE: 16

| | |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tcggttatgg tcttcaatgc tttgcaagat acccagatca tatgaaacgg | 240 |
| catgactttt tcaagagtgc catgcccgaa ggttatgttc aggaaagaac tatattttc | 300 |
| aaagatgacg ggaactacaa gacacgtgct gaagtcaagt ttgaaggtga taccttgtt | 360 |
| aatagaatcg agttaaaagg tattgatttt aagaagatg gaaacattct tggacacaaa | 420 |
| ttggaataca actataactc aggcaatgta tacatcatgg cagacaaaca aaagaatgga | 480 |
| atcaaagtta acttcaaaat tagacacaac attgaagatg gaagcgttca actagcagac | 540 |
| cattatcaac aaaatactcc aattggcgat ggccctgtcc ttttaccaga caaccattac | 600 |
| ctgtcctatc aatctgccct ttcgaaagat cccaacgaaa agagagacca catggtcctt | 660 |
| cttgagtttg taacagctgc tgggattaca catggcatgg atgaactata caaa | 714 |

<210> SEQ ID NO 17
<211> LENGTH: 714
<212> TYPE: DNA
<213> ORGANISM: Aequorea victoria

<400> SEQUENCE: 17

| | |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tcggttatgg tcttcaatgc tttgcaagat acccagatca tatgaaacgg | 240 |
| catgactttt tcaagagtgc catgcccgaa ggttatgttc aggaaagaac tatattttc | 300 |
| aaagatgacg ggaactacaa gacacgtgct gaagtcaagt ttgaaggtga taccttgtt | 360 |
| aatagaatcg agttaaaagg tattgatttt aagaagatg gaaacattct tggacacaaa | 420 |
| ttggaataca actataactc acagaatgta tacatcatgg cagacaaaca aaagaatgga | 480 |
| atcaaagtta acttcaaaat tagacacaac attgaagatg gaagcgttca actagcagac | 540 |

-continued

| cattatcaac | aaaatactcc | aattggcgat | ggccctgtcc | ttttaccaga | caaccattac | 600 |
| ctgtcctatc | aatctgccct | ttcgaaagat | cccaacgaaa | agagagacca | catggtcctt | 660 |
| cttgagtttg | taacagctgc | tgggattaca | catggcatgg | atgaactata | caaa | 714 |

<210> SEQ ID NO 18
<211> LENGTH: 720
<212> TYPE: DNA
<213> ORGANISM: Aequorea victoria

<400> SEQUENCE: 18

| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcgtgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagcggcaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaagtaa | 720 |

<210> SEQ ID NO 19
<211> LENGTH: 720
<212> TYPE: DNA
<213> ORGANISM: Aequorea victoria

<400> SEQUENCE: 19

| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcgtgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccagaac | gtctatatca | tggccgacaa | gcagaagaac | 480 |
| ggcatcaagg | tgaacttcaa | gatccgccac | aacatcgagg | acggcagcgt | gcagctcgcc | 540 |
| gaccactacc | agcagaacac | ccccatcggc | gacggccccg | tgctgctgcc | cgacaaccac | 600 |
| tacctgagct | accagtccgc | cctgagcaaa | gaccccaacg | agaagcgcga | tcacatggtc | 660 |
| ctgctggagt | tcgtgaccgc | cgccgggatc | actctcggca | tggacgagct | gtacaagtaa | 720 |

<210> SEQ ID NO 20
<211> LENGTH: 5
<212> TYPE: PRT
<213> ORGANISM: Homo sapiens

<400> SEQUENCE: 20

```
Lys Lys Lys Arg Lys
1               5
```

<210> SEQ ID NO 21
<211> LENGTH: 26
<212> TYPE: PRT
<213> ORGANISM: Homo sapiens

<400> SEQUENCE: 21

```
Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25
```

<210> SEQ ID NO 22
<211> LENGTH: 4
<212> TYPE: PRT
<213> ORGANISM: Homo sapiens

<400> SEQUENCE: 22

```
Lys Asp Glu Leu
1
```

<210> SEQ ID NO 23
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 23

```
Cys Ala Ala Xaa
1
```

<210> SEQ ID NO 24
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 24

```
Cys Cys Xaa Xaa
1
```

<210> SEQ ID NO 25
<211> LENGTH: 26
<212> TYPE: PRT
<213> ORGANISM: Oryctolagus cuniculus

<400> SEQUENCE: 25

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 26
<211> LENGTH: 20
<212> TYPE: PRT
<213> ORGANISM: Meleagris gallopavo

<400> SEQUENCE: 26

```
Ala Arg Arg Lys Trp Gln Lys Thr Gly His Ala Val Arg Ala Ile Gly
 1               5                  10                  15

Arg Leu Ser Ser
            20
```

<210> SEQ ID NO 27
<211> LENGTH: 20
<212> TYPE: PRT
<213> ORGANISM: Rattus norvegicus

<400> SEQUENCE: 27

```
Ala Arg Arg Lys Leu Lys Gly Ala Ile Leu Thr Thr Met Leu Ala Thr
 1               5                  10                  15

Arg Asn Phe Ser
            20
```

<210> SEQ ID NO 28
<211> LENGTH: 17
<212> TYPE: PRT
<213> ORGANISM: Gallus gallus

<400> SEQUENCE: 28

```
Gly Val Arg Asn Ile Lys Ser Met Trp Glu Lys Gly Asn Val Phe Ser
 1               5                  10                  15

Ser
```

<210> SEQ ID NO 29
<211> LENGTH: 20
<212> TYPE: PRT
<213> ORGANISM: Rattus norvegicus

<400> SEQUENCE: 29

```
Ala Arg Arg Lys Leu Lys Ala Ala Val Lys Ala Val Val Ala Ser Ser
 1               5                  10                  15

Arg Leu Gly Ser
            20
```

<210> SEQ ID NO 30
<211> LENGTH: 26
<212> TYPE: PRT
<213> ORGANISM: Oryctolagus cuniculus

<400> SEQUENCE: 30

```
Phe Met Asn Asn Trp Glu Val Tyr Lys Leu Leu Ala His Ile Arg Pro
 1               5                  10                  15

Pro Ala Pro Lys Ser Gly Ser Tyr Thr Val
            20                  25
```

<210> SEQ ID NO 31
<211> LENGTH: 24
<212> TYPE: PRT
<213> ORGANISM: Bos taurus

<400> SEQUENCE: 31

```
Ala Arg Lys Glu Val Ile Arg Asn Lys Ile Arg Ala Ile Gly Lys Met
 1               5                  10                  15

Ala Arg Val Phe Ser Val Leu Arg
            20
```

<210> SEQ ID NO 32
<211> LENGTH: 26

```
<212> TYPE: PRT
<213> ORGANISM: Oryctolagus cuniculus

<400> SEQUENCE: 32

Leu Arg Arg Leu Ile Asp Ala Tyr Ala Phe Arg Ile Tyr Gly His Trp
 1               5                  10                  15

Val Lys Lys Gly Gln Gln Gln Asn Arg Gly
            20                  25

<210> SEQ ID NO 33
<211> LENGTH: 27
<212> TYPE: PRT
<213> ORGANISM: Oryctolagus cuniculus

<400> SEQUENCE: 33

Arg Gly Lys Phe Lys Val Ile Cys Leu Thr Val Leu Ala Ser Val Arg
 1               5                  10                  15

Ile Tyr Tyr Gln Tyr Arg Arg Val Lys Pro Gly
            20                  25

<210> SEQ ID NO 34
<211> LENGTH: 28
<212> TYPE: PRT
<213> ORGANISM: Homo sapiens

<400> SEQUENCE: 34

Leu Arg Arg Gly Gln Ile Leu Trp Phe Arg Gly Leu Asn Arg Ile Gln
 1               5                  10                  15

Thr Gln Ile Lys Val Val Asn Ala Phe Ser Ser Ser
            20                  25

<210> SEQ ID NO 35
<211> LENGTH: 21
<212> TYPE: PRT
<213> ORGANISM: Bos taurus

<400> SEQUENCE: 35

Arg Arg Lys His Leu Gln Arg Pro Ile Phe Arg Leu Arg Cys Leu Val
 1               5                  10                  15

Lys Gln Leu Glu Lys
            20

<210> SEQ ID NO 36
<211> LENGTH: 21
<212> TYPE: PRT
<213> ORGANISM: Bos taurus

<400> SEQUENCE: 36

Thr Glu Lys Met Trp Gln Arg Leu Lys Gly Ile Leu Arg Cys Leu Val
 1               5                  10                  15

Lys Gln Leu Glu Lys
            20

<210> SEQ ID NO 37
<211> LENGTH: 23
<212> TYPE: PRT
<213> ORGANISM: Rattus norvegicus

<400> SEQUENCE: 37

Lys Arg Arg Ala Ile Gly Phe Lys Leu Ala Glu Ala Val Lys Phe
 1               5                  10                  15

Ser Ala Lys Leu Met Gly Gln
```

<210> SEQ ID NO 38
<211> LENGTH: 28
<212> TYPE: PRT
<213> ORGANISM: Bos taurus

<400> SEQUENCE: 38

Ile Lys Pro Ala Lys Arg Met Lys Phe Lys Thr Val Cys Tyr Leu Leu
 1               5                  10                  15

Val Gln Leu Met His Cys Arg Lys Met Phe Lys Ala
            20                  25

<210> SEQ ID NO 39
<211> LENGTH: 20
<212> TYPE: PRT
<213> ORGANISM: Bordetella pertussin

<400> SEQUENCE: 39

Ile Asp Leu Leu Trp Lys Ile Ala Arg Ala Gly Ala Arg Ser Ala Val
 1               5                  10                  15

Gly Thr Glu Ala
            20

<210> SEQ ID NO 40
<211> LENGTH: 27
<212> TYPE: PRT
<213> ORGANISM: Homo sapiens

<400> SEQUENCE: 40

Lys Ala His Lys Ala Ala Thr Lys Ile Gln Ala Ser Phe Arg Gly His
 1               5                  10                  15

Ile Thr Arg Lys Lys Leu Lys Gly Glu Lys Lys
            20                  25

<210> SEQ ID NO 41
<211> LENGTH: 24
<212> TYPE: PRT
<213> ORGANISM: Homo sapiens

<400> SEQUENCE: 41

Lys Thr Ala Ser Pro Trp Lys Ser Ala Arg Leu Met Val His Thr Val
 1               5                  10                  15

Ala Thr Phe Asn Ser Ile Lys Glu
            20

<210> SEQ ID NO 42
<211> LENGTH: 25
<212> TYPE: PRT
<213> ORGANISM: Rattus norvegicus

<400> SEQUENCE: 42

Lys Lys Lys Lys Lys Arg Phe Ser Phe Lys Lys Ser Phe Lys Leu Ser
 1               5                  10                  15

Gly Phe Ser Phe Lys Lys Ser Lys Lys
            20                  25

<210> SEQ ID NO 43
<211> LENGTH: 24
<212> TYPE: PRT
<213> ORGANISM: Mus musculus

<400> SEQUENCE: 43

```
Lys Lys Lys Lys Lys Phe Ser Phe Lys Lys Pro Phe Lys Leu Ser Gly
 1               5                  10                  15

Leu Ser Phe Lys Arg Asn Arg Lys
            20
```

<210> SEQ ID NO 44
<211> LENGTH: 31
<212> TYPE: PRT
<213> ORGANISM: Homo sapiens

<400> SEQUENCE: 44

```
Lys Gln Gln Lys Glu Lys Thr Arg Trp Leu Asn Thr Pro Asn Thr Tyr
 1               5                  10                  15

Leu Arg Val Asn Val Ala Asp Glu Val Gln Arg Asn Met Gly Ser
            20                  25                  30
```

<210> SEQ ID NO 45
<211> LENGTH: 21
<212> TYPE: PRT
<213> ORGANISM: Mus musculus

<400> SEQUENCE: 45

```
Lys Asp Gln Val Ala Asn Ser Ala Phe Gln Glu Arg Leu Arg Lys His
 1               5                  10                  15

Gly Leu Glu Val Ile
            20
```

<210> SEQ ID NO 46
<211> LENGTH: 21
<212> TYPE: PRT
<213> ORGANISM: Human immunodeficiency virus type 1

<400> SEQUENCE: 46

```
Tyr His Arg Leu Arg Asp Leu Leu Leu Ile Val Lys Arg Ile Val Glu
 1               5                  10                  15

Leu Leu Gly Arg Arg
            20
```

<210> SEQ ID NO 47
<211> LENGTH: 23
<212> TYPE: PRT
<213> ORGANISM: Bos taurus

<400> SEQUENCE: 47

```
Gln Gln Leu Ala Thr Leu Ile Gln Lys Thr Tyr Arg Gly Trp Arg Cys
 1               5                  10                  15

Arg Thr His Tyr Gln Leu Met
            20
```

<210> SEQ ID NO 48
<211> LENGTH: 24
<212> TYPE: PRT
<213> ORGANISM: Mus musculus

<400> SEQUENCE: 48

```
Arg Ala Ala Cys Ile Arg Ile Gln Lys Thr Ile Arg Gly Trp Leu Leu
 1               5                  10                  15

Arg Lys Arg Tyr Leu Cys Met Gln
            20
```

<210> SEQ ID NO 49

```
<211> LENGTH: 14
<212> TYPE: PRT
<213> ORGANISM: Vespa crabro

<400> SEQUENCE: 49

Ile Asn Leu Lys Ala Leu Ala Ala Leu Ala Lys Lys Ile Leu
1               5                   10

<210> SEQ ID NO 50
<211> LENGTH: 26
<212> TYPE: PRT
<213> ORGANISM: Apis mellifera

<400> SEQUENCE: 50

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 51
<211> LENGTH: 30
<212> TYPE: PRT
<213> ORGANISM: Bos taurus

<400> SEQUENCE: 51

His Ser Gln Gly Thr Phe Thr Thr Ser Asp Tyr Ser Lys Tyr Leu Asp
1               5                   10                  15

Ser Arg Arg Ala Gln Asp Phe Val Gln Trp Leu Met Asn Thr
            20                  25                  30

<210> SEQ ID NO 52
<211> LENGTH: 27
<212> TYPE: PRT
<213> ORGANISM: Sus scrofa

<400> SEQUENCE: 52

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25

<210> SEQ ID NO 53
<211> LENGTH: 28
<212> TYPE: PRT
<213> ORGANISM: Homo sapiens

<400> SEQUENCE: 53

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 54
<211> LENGTH: 33
<212> TYPE: PRT
<213> ORGANISM: Sus scrofa

<400> SEQUENCE: 54

Tyr Ala Asp Gly Thr Phe Ile Ser Asp Tyr Ser Ala Ile Met Asn Lys
1               5                   10                  15

Ile Arg Gln Gln Asp Phe Val Asn Trp Leu Leu Ala Gln Gln Lys
            20                  25                  30
```

Ser

```
<210> SEQ ID NO 55
<211> LENGTH: 17
<212> TYPE: PRT
<213> ORGANISM: Artificial Sequence
<220> FEATURE:
<223> OTHER INFORMATION: Calmodulin binding peptide-2

<400> SEQUENCE: 55

Lys Leu Trp Lys Lys Leu Leu Lys Leu Leu Lys Leu Leu Lys Leu
 1               5                  10                  15

Gly

<210> SEQ ID NO 56
<211> LENGTH: 5
<212> TYPE: PRT
<213> ORGANISM: Artificial Sequence
<220> FEATURE:
<223> OTHER INFORMATION: Linker moiety; sequence repeated indefinitely

<400> SEQUENCE: 56

Gly Gly Gly Gly Ser
 1               5

<210> SEQ ID NO 57
<211> LENGTH: 12
<212> TYPE: PRT
<213> ORGANISM: Artificial Sequence
<220> FEATURE:
<223> OTHER INFORMATION: Linker moiety

<400> SEQUENCE: 57

Gly Lys Ser Ser Gly Ser Gly Ser Glu Ser Lys Ser
 1               5                  10

<210> SEQ ID NO 58
<211> LENGTH: 14
<212> TYPE: PRT
<213> ORGANISM: Artificial Sequence
<220> FEATURE:
<223> OTHER INFORMATION: Linker moiety

<400> SEQUENCE: 58

Gly Ser Thr Ser Gly Ser Gly Lys Ser Ser Glu Gly Lys Gly
 1               5                  10

<210> SEQ ID NO 59
<211> LENGTH: 18
<212> TYPE: PRT
<213> ORGANISM: Artificial Sequence
<220> FEATURE:
<223> OTHER INFORMATION: Linker moiety

<400> SEQUENCE: 59

Gly Ser Thr Ser Gly Ser Gly Lys Ser Ser Glu Gly Ser Gly Ser Thr
 1               5                  10                  15

Lys Gly

<210> SEQ ID NO 60
<211> LENGTH: 14
<212> TYPE: PRT
<213> ORGANISM: Artificial Sequence
<220> FEATURE:
<223> OTHER INFORMATION: Linker moiety
```

-continued

```
<400> SEQUENCE: 60

Gly Ser Thr Ser Gly Ser Gly Lys Ser Ser Glu Gly Lys Gly
1               5                   10

<210> SEQ ID NO 61
<211> LENGTH: 18
<212> TYPE: PRT
<213> ORGANISM: Artificial Sequence
<220> FEATURE:
<223> OTHER INFORMATION: Linker moiety

<400> SEQUENCE: 61

Gly Ser Thr Ser Gly Ser Gly Lys Pro Gly Ser Gly Glu Gly Ser Thr
1               5                   10                  15

Lys Gly

<210> SEQ ID NO 62
<211> LENGTH: 14
<212> TYPE: PRT
<213> ORGANISM: Artificial Sequence
<220> FEATURE:
<223> OTHER INFORMATION: Linker moiety

<400> SEQUENCE: 62

Glu Gly Lys Ser Ser Gly Ser Gly Ser Glu Ser Lys Glu Phe
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Linker moiety

<400> SEQUENCE: 63

Gly Gly Thr Gly Gly Ser
1               5
```